US007799955B2

(12) United States Patent
Joannou

(10) Patent No.: US 7,799,955 B2
(45) Date of Patent: *Sep. 21, 2010

(54) ISOFLAVONE METABOLITES

(75) Inventor: George Eustace Joannou, Double Bay (AU)

(73) Assignee: Michael Ruane, Ardross (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/413,702

(22) Filed: Mar. 30, 2009

(65) Prior Publication Data

US 2009/0209655 A1 Aug. 20, 2009

Related U.S. Application Data

(63) Continuation of application No. 12/023,581, filed on Jan. 31, 2008, now abandoned, which is a continuation of application No. 11/132,025, filed on May 18, 2005, now abandoned, which is a continuation of application No. 10/018,308, filed as application No. PCT/AU00/00392 on May 1, 2000, now Pat. No. 7,056,952.

(30) Foreign Application Priority Data

Apr. 30, 1999 (AU) .................................... PQ0082

(51) Int. Cl.
 C07C 49/00 (2006.01)
 A61K 31/12 (2006.01)
(52) U.S. Cl. ...................................... 568/331; 514/685
(58) Field of Classification Search ................. 568/331; 514/685
See application file for complete search history.

(56) References Cited

U.S. PATENT DOCUMENTS

| 5,352,384 A | 10/1994 | Shen |
| 6,818,668 B2 | 11/2004 | Roberts |

FOREIGN PATENT DOCUMENTS

| EP | 0129667 | 4/1984 |
| WO | WO 03/087083 | 10/2003 |

OTHER PUBLICATIONS

Hu et al. Drug metabolism and disposition, 31 (7), 924-931, 2003.*
Klus et al. Arch Microbiol.,164, 428-434, 1995.*
George E. Joannou et al., *15β-Hydroxysteroids (Part III). Steroids of the human perinatal period: The synthesis of 3β, 15 β, 17 α -trihydroxy-5-pregnen-20-one. Application of nutyl boronic acid protections of a 17,20-glycol*, (1996) Steroids, vol. 61, pp. 11-17.
Graham E. Kelly et al., *Metabolites of dietary (soya) isoflavones in human urine*, (1993) Clin. Chim. Acta 223 (Elsevier Science Publishers B.V.), pp. 9-22.
Kikkoman Corp, *Simple and convenient isolation of genistein from isoflavone mixt. by selective extraction with chloro-hydrocarbon*, (Jul. 1995) 95-272884/36.

Andreas Constantinou et al., *Flavonoids as DNA Topoisomerase Antagonists and Poisons: Structure-Activity Relationships*, (Feb. 1995) Journal of Natural Products, vol. 58, No. 2, pp. 217-225.
K. Murata, *Antioxidative Stability of Tempeh*, (May 1998), JAOCS, vol. 65, No. 5, pp. 799-800.
Karlis Briviba, *Isoflavonoids as Inhibitors of Lipid Peroxidation and Quenchers of Singlet Oxygen*, Collection of the National Library of Medicine (Lipid Peroxidation and Quenchers of Singlet Oxygen), Ch. 12, pp. 295-302.
Martin Weidenborner et al., *Structure-activity relationships among isoflavonoids with regard to their antifungal properties*, (1994) Mycol. Res. 98 (12), pp. 1376-1378.
Mustafa Bulut, *Neue Synthese von Isoflavenen und Vergleichende Untersuchengen Threr Abkommlinge Bezuglich Ihrer Pharmakologischen Eigenshaften*, (1991) Chimica Acta Turcica 19.
Cornelia Voss, *New Isoflavonoids as Inhibitors of Porchine 5-Lipooxygenase*, (1992) Biochemical Pharmacology, vol. 44, No. 1, pp. 157-162.
M. Weidenborner et al., *Control of Storage Fungi of the Genus Aspergillus on Legumes with Flavonoids and Isoflavonoids*, (1990) Angew. Botanik 64, pp. 175-190.
Martin Weidenborner et al., *Antifungal Activity of Isoflavonoids in Different Reduced Stages on Rhizoctonia solani and Sclerotium rolfsii*, (1990) Phytochemistry, vol. 29, No. 3, pp. 801-903.
Martin Weidenborner et al., *Antifungal Activity of Isoflavonoids Against Storage Fungi of the Genus Aspergillus*, (1989) Phytochemistry, vol. 28, No. 12, pp. 3317-3319.
Montandon, J.B. et al., *In-Vitro versus In-Vito Activities of new 5-lipoxygenase Inhibitors with Antiinflamatory Activity*, (1989) Int. J. Tiss. Reac. XI(3) pp. 107-112.
Werner Seeger et al., *Effects of alpha-tocopherol, its carboxylic acid chromane compund and two novel antioxidant isoflavones on prostaglandin H synthase activity and autodeactivation*, (1988) Naunyn-Schmiedeberg's Arech Pharmacol 338, pp. 74-81.
M. Weidenborner et al., *Fungizide wirking von isoflavonoiden auf schimmelpilze der gattung aspergillus*, (1987) Med. Fac. Lanbouww. Rijksuniv. Gent 52(3a), pp. 933-942.

(Continued)

*Primary Examiner*—D. Margaret Seaman
*Assistant Examiner*—Nizal S Chandrakumar
(74) *Attorney, Agent, or Firm*—Barnes & Thornburg LLP

(57) ABSTRACT

There are disclosed compounds of formulae (I) or (II) in which A is selected from the group consisting of (1), (2), (3) and (4); OH, and one of $R_1$ and $R_2$ is selected from H, OH and $OCH_3$, and the other of $R_1$ and $R_2$ is selected from OH and $OCH_3$; one of R3 and R4 is selected from H, OH and OCH3, and the other of R3 and R4 is selected from OH and OCH3; provided that at least one of the pairs $R_1$, $R_2$ and $R_3$, $R_4$ are both OH; $R_5$ is selected from OH and $OCH_3$; and ----- denotes a single or double bond; and pharmaceutically acceptable salts and prodrugs thereof. The compounds of the invention are useful for the treatment of hormone-dependent conditions and cancers.

12 Claims, No Drawings

OTHER PUBLICATIONS

P. Kuhl et al., *6,7,4'-Trihydroxyisoflavan: A potent and selective inhibitor of 5-lipoxygenase in human and porcine peripheral blood leukocytes*, (Dec. 1984) Prostaglandins, vol. 28, No. 6, pp. 783-805.

Rainer Philipp Kramer et al., *Antifungal activity of soybean and chickpea isoflavones and their reduced derivatives*, (Mar. 1984) Phytochemistry, vol. 23, No. 10, pp. 2203-2205.

H. Adlercreutz et al., *The New Biology of Steroid Hormones*, (1991) Serono Symposia Publications (fr. Raven Press), pp. 145-156.

Tetsu Akiyama et al., *Genistein, a Specific Inhibitor of Tyrosine-specific Protein Kinases*, (1987) The Journal of Biological Chemistry, vol. 262, No. 12, Apr. 25 issue, pp. 5592-5595.

Lewis C. Cantley et al., *Oncogenes and Signal Transduction*, (1991) Cell, Col. 64, pp. 281-302.

Lori Coward et al., *Genistein, Daidzein, and Their β-Glycoside Conjugates: Antitumor Isoflavones in Soybean Foods from American and Asian Diets*, (1993) J. Agric. Food Chem., 41, pp. 1961-1967.

Junko Ebata et al., *β-Glucosidase Involved in the Antioxidant Formation in Tempeh, Fermented Soybeans*, (1972) Faculty of the Science of Living, Osaka City University, pp. 323-329.

Shinji Funayama et al., *Structural Study of Isoflavonoids Possessing Antioxidant Activity Isolated from the Fermentation Broth of Streptomyces sp.*, (Sep. 1989) The Journal of Antibiotics, vol. XLII, No. 9, pp. 1350-1355.

Toshihiko Hirano et al., *Antiproliferative Effects of Synthetic and Naturally Occurring Flavonoids on Tumor Cells of the Human Breast Carcinoma Cell Line, ZR-75-1*, (Apr. 1989) Reasearch Communications in Chemical Pathology and Pharmacology, vol. 64, No. 1, pp. 69-78.

Sylvia Keuth et al., *Vitamin $B_{12}$ Production by Citrobacter freundii or Klebsiella pneumonia during Tempeh Fermentation and Proof of Enterotoxin Absence by PCR*, (1994) Applied and Environmental Microbiology, vol. 60, pp. 1495-1499.

Shigemitsu Kudou et al., *Malonyl Isoflavone Glycosides in Soybean Seeds (Glycine max Merrill)*, (1991) Agric. Biol. Chem., 55 (9), pp. 2227-2233.

Kanki Komiyama et al., *Isolation of Isoflavonoids Possessing Antioxidant Activity from the Fermentation Broth of Streptomyces sp.*, (Sep. 1989) The Journal of Antibiotics, vol. XLII, No. 9, pp. 1344-1349.

Makoto Makishima et al., *Effects of Inhibitors of Protein Tyrosine Kinase Activity and/or Phosphatidylinositol Turnover on Differentiation of Some Human Myelomonocytic Leukemia Cells*, (1991) Leukemia Research, vol. 15, No. 8, pp. 701-708.

Elliott Middleton, Jr. et al., *Commentary: Effects of Flavonoids on Immune and Inflammatory Cell Functions*, (1992) Biochemical Pharmacology, vol. 43, No. 6, pp. 1167-1179.

Michael Naim et al., *Soybean Isoflavones, Characterization, Determination, and Antifungal Activity*, (1974) J. Agr. Food Chem., vol. 22, No. 5, pp. 806-810.

Greg Peterson et al., *Genistein Inhibition of the Growth of Human Breast Cancer Cells: Independence from Estrogen Receptors and the Multi-drug Resistance Gene*, (Aug. 1991) Biochemical and Biophysical Research Communications, vol. 179, No. 1, pp. 661-667.

Cornelia Voss et al., *New Isoflavonoids as Inhibitors of Porcine 5-lipoxygenase*, (1992) Biochemical Pharmacology, vol. 44, No. 1, pp. 157-162.

Surendra P. Verma et al., *Effect of Soy-Derived Isoflavonoids on the Induced Growth of MCF-7 Cells by Estrogenic Environmental Chemicals*, (1998) Nutrition and Cancer, 30(3), Lawrence Erlbaum Associates, Inc., pp. 232-239.

K. Mackenbrock et al., *3'-Hydroxylation of 4'-Methoxyisoflavones by Fusarium oxysporum f. lycopersici*, (1983) Z. Naturforsch 38c, pp. 708-710.

Hideo Chimura et al., *New Isoflavones, Inhibiting Catechol-o-methyltransferase Produced by Streptomyces*, (Sep. 1975) The Journal of Antibiotics, vol. XXVIII, No. 9, pp. 619-626.

Answers 1-19 CA Copyright 2000 ACS.

Waehaelae, K., et al., *The Synthesis, Structure and Anticancer Activity of cis- and trans-4', 7-Dihydroxyisoflavan-4-ols*, (1998) CA 127:307275.

Bulut, Mastafa, *Synthesis and antioxidant activity of isoflavones and isoflavanones*, (1993) CA 118:124232.

Hu, M., et al., *Identification of CYP1A2 as the Main Isoform for the Phase i Hydroxylated Metabolism of Genistein and a Prodrug Converting Enzyme of Methylated Isoflavones*, Drug Metabolism and Disposition, vol. 31, No. 7, pp. 924-931.

Setchell, K., et al., *Bioavailability of Nutrients and Other Bioactive Components from Dietary Supplements*, The Journal of Nutrition, Apr. 2001, 4S, Research Library, pp. 1362-1375.

\* cited by examiner

ISOFLAVONE METABOLITES

CROSS-REFERENCE TO RELATED APPLICATIONS

This application is a continuation of U.S. Ser. No. 12/023,581 filed Jan. 31, 2008 now abandonded. U.S. Ser. No. 12/023,581 is a continuation of U.S. Ser. No. 11/132,025 filed May 18, 2005, now abandoned. U.S. Ser. No. 11/132,025 is a continuation of U.S. Ser. No. 10/018,308 filed Jan. 24, 2004, now U.S. Pat. No. 7,056,952. U.S. Ser. No. 10/018,308 is the U.S. national phase of PCT/AU00/00392 filed May 1, 2000. PCT/AU00/00392 claims priority to Australian provisional application serial no. PQ0082 filed Apr. 30, 1999. The disclosures of U.S. Ser. No. 12/023,581, U.S. Ser. No. 11/132,025, U.S. Ser. No. 10/018,308, PCT/AU00/00392 and Australian provisional application serial no. PQ0082 are all incorporated herein by reference.

FIELD OF THE INVENTION

This invention relates to certain isoflavonoid compounds, compositions containing the same, and therapeutic uses of those compounds.

BACKGROUND OF THE INVENTION

In recent years there has been increasing attention on phytoestrogens particularly isoflavonoids. Isoflavonoids or isoflavones (as they are also known) are a class of phytooestrogens which are found in plants and which are based on a diphenolic ring structure. Due to their structure, it has been documented that they are able to bind to oestrogen receptors on animals including humans. A small subgroup of isoflavones are known to display oestrogenic activity, as well as anti-carcinogenic, antifungal, antiproliferative properties and anti-oxidative effects. These oestrogenic isoflavones (genistein, biochanin, daidzein, glycitein and formononetin) are predominantly found in plants which are members of the Leguminosae family.

Most legumes have been found to contain at least one or more of these oestrogenic isoflavones, with the richest sources being soya beans, lentils, clover, chick peas, alfalfa and other beans. Most human diets contain low to moderate levels of oestrogenic isoflavones. In typical diets in developed Western countries, the dietary intake of the oestrogenic isoflavones is low and often negligible, as legumes are not relied upon strongly as a source of protein, being instead replaced by animal products.

However, the dietary intake of oestrogenic isoflavones from traditional diets of Eastern and developing countries such as India, China and South America is moderate to high, given the fairly high dietary intake of beans including soya beans, kidney beans, lima beans, broad beans, butter beans, chick peas and lentils. The presence of such dietary levels of oestrogenic isoflavones is confirmed by detection of the amounts of the isoflavones daidzein, genistein, glycitein, formononetin and biochanin and their metabolites in human urine. People with high legume intake in their diets excrete substantially higher amounts of isoflavone metabolites in their urine than people with largely omnivorous or low-legume diets.

After ingestion, isoflavones undergo varying degrees of metabolism within the digestive system. The naturally occurring, water soluble glycosidic form of isoflavone undergoes hydrolysis to the aglycone form in the gut, while biochanin and formononetin are demethylated by bacterial fermentation to genistein and daidzein respectively. It appears that the majority of the aglycone isoflavones then undergo fermentation by intestinal bacteria to produce end products including equol, dehydroequol, O-desmethylangolensin (ODMA), dihydrodaidzein, tetra-hydrodaidzein and dihydrogenistein. The isoflavones, their metabolites and derivatives circulate around the body and are mainly excreted in the urine, in which they can then be detected.

As stated above, given the presence of high levels of isoflavones in legumes, particularly soya beans, and the knowledge that the isoflavones are fermented or metabolised by intestinal or bowel bacteria to produce isoflavone metabolites, research has been conducted into microbial fermentations of soybeans and has demonstrated production of metabolites including 6,7,4'-trihydroxyisoflavone (hereinafter called Factor 2) and other polyhydroxylated isoflavonoids.

Traditional Asian food products such as tempeh, tofu, miso etc are foods produced from soybeans by fermentation mainly by fungi of the genus *Rhizopus*. It has been shown that several bacteria species may also be involved in tempeh production. For traditional tempeh fermentation, the soybeans are cooked, dehulled and soaked overnight. A spontaneous bacterial acidification occurs during this phase. In industrial tempeh fermentation processes, the cooked soybeans are acidified with lactic acid. After the soaking process, the soybeans are cooked again and incubated with microbial inocula for 2 days.

In unfermented soybeans, the isoflavones genistein, daidzein and glycitein predominantly occur as isoflavone glucosides and acylglucosides. It has been shown that during tempeh fermentation, the isoflavone aglycones are liberated from the conjugates and accumulate in the tempeh product. Further findings have shown that during fermentation the isoflavone 6,7,4'-trihydroxyisoflavone (termed "Factor 2" by Gyorgy et al. in *Nature* (1964) 203. 870-872), also accumulates.

It was previously thought that the fungi of the genus *Rhizopus* were responsible for the formation of Factor 2 from either daidzein or glycitein. However, subsequent studies on the metabolism of daidzein and glycitein by Klus et al., 1993 showed that isolates of *Brevibacterium epidermidis* and *Micrococcus luteus*, which were isolated from Indonesian tempeh samples, readily transform glycitein, forming Factor 2. A third tempeh-derived bacterium, *Microbacterium arborescens*, metabolized daidzein, producing both Factor 2 and glycitein. More recently, Klus, K. and Barz, W. *Arch. Microbiol.* 164:428-434, (1995) investigated five other bacterial isolates, which were isolated from tempeh samples containing Factor 2 and were classified as *Micrococcus* or *Arthrobacter* strains, for their ability to metabolize daidzein and glycitein by hydroxylation or O-demethylation reactions. Their results show that a number of polyhydroxylated isoflavones were formed, hydroxylated at three or four of positions 6, 7, 8, 3' and 4'. Of these Factor 2 was the major product produced by most of the microbial strains. The bacterial strains only hydroxylated but did not degrade the substrates namely daidzein or glycitein. The compounds of the present invention were not identified by Klus and Barz, however, Various polyhydroxylated isoflavones known in the prior art are known to exhibit anti-inflammatory and anti-allergenic activity and to express anticarcinogenic properties due inhibition of protein tyrosine kinases, which play a key role in cellular pathways in tumour cell growth. In in vitro tests, these isoflavones also inhibit the growth of human leukemia (Makishima et al., 1991) and human breast cancer cells (Hirano et al, 1989; Peterson and Barnes, 1991). In essence, the polyhydroxylated isoflavones occurring as dietary factors in fermented soybean products are putative causes of the lower incidence of cancer-related diseases in Asian populations, and have been used in the treatment of a variety of cancers including breast cancer, ovarian cancer, large bowel cancer; and prostatic cancer.

Other therapeutic uses of the oestrogenic isoflavones which have been disclosed include their use as therapeutics for menopausal symptoms and osteoporosis (WO 98/50026, European patent application 0135172, U.S. Pat. No. 5,498,631 in the name of Gorbach et al); pre-menstrual symptoms; Reynauds Syndrome; rheumatic diseases; Buergers Disease; coronary artery spasm; migraine headaches; benign prostatic hypertrophy and hypertension.

As stated above, isoflavonoids are natural plant compounds which possess antitumorigenic properties. Of all oestrogenic isoflavones of which daidzein, genistein, formononetin and biochanin-A are the most well known, it has been shown that individually, genistein is the most potent inhibitor (IC50=25-33 μM) of the proliferation of MCF-7 cells induced by a number of environmental chemicals such as 1-(o-chlorophenyl)-1-(p-chlorophenyl)-2,2,2-trichloroethane, 5-octylphenol and 4-nonylphenol as demonstrated recently by Verma S P and Goldin B R (*Nutrition & Cancer* 30(3):232-9. 1998).

The same authors also noted that a mixture of isoflavones was the most potent inhibitor against the induced proliferation. However, as in the case of other research workers they found that genistein, biochanin A, equol and to some extent daidzein at <10 μM can enhance the growth of MCF-7 cells.

There is therefore a need for novel isoflavonoids which can inhibit the proliferation of cancer cells but which do not enhance their growth at low concentrations, and which exhibit other therapeutic properties.

OBJECTS OF THE INVENTION

It is therefore an object of the present invention to provide novel isoflavonoid compounds.

It is another object of the present invention to provide compositions including food and drink compositions containing novel isoflavonoid compounds.

It is a further object of the present invention to utilise novel isoflavonoid compounds in treating hormone dependent conditions and other diseases and disorders.

SUMMARY OF THE INVENTION

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers.

According to a first aspect of the present invention there is provided a compound of formula I or formula II

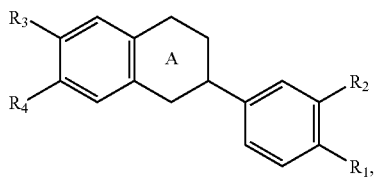
(I)

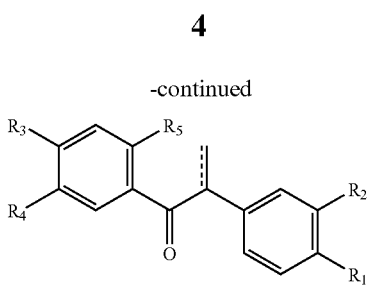
(II)

in which
A is selected from the group consisting of

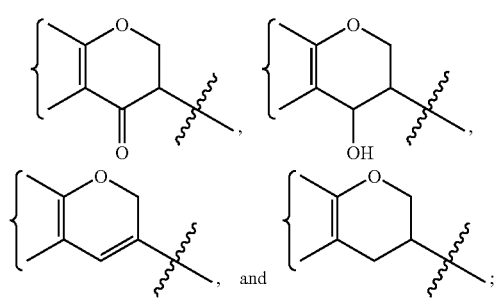

one of $R_1$ and $R_2$ is selected from H, OH and $OCH_3$, and the other of $R_1$ and $R_2$ is selected from OH and $OCH_3$;
one of $R_3$ and $R_4$ is selected from H, OH and $OCH_3$, and the other of $R_3$ and $R_4$ is selected from OH and $OCH_3$;
provided that at least one of the pairs $R_1$, $R_2$ and $R_3$, $R_4$ are both OH;
$R_5$ is selected from OH and $OCH_3$; and
----- denotes a single or double bond,
or a pharmaceutically acceptable salt or prodrug thereof.

In one form, the invention relates to compounds of formula (I) or (II) as defined hereinabove, wherein
one of $R_1$ and $R_2$ is selected from H and OH, and the other of $R_1$ and $R_2$ is OH;
one of $R_3$ and $R_4$ is selected from H and OH, and the other of $R_3$ and $R_4$ is OH;
provided that at least one of the pairs $R_1$, $R_2$ and $R_3$, $R_4$ are both OH;
$R_5$ is OH; and
----- denotes a single or double bond.

In another form, the invention relates to compounds of the formula (IA) or (IIA)

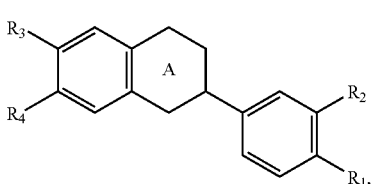
(IA)

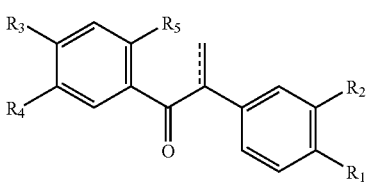
(IIA)

wherein A is as defined hereinabove
$R_2$ is H, and $R_1$ is selected from OH and $OCH_3$;
$R_3$ and $R_4$ are each OH;
$R_5$ is selected from OH and $OCH_3$; and
----- denotes a single or double bond.

In a further form, the invention relates to compounds of the formula (IB) or (IIB)

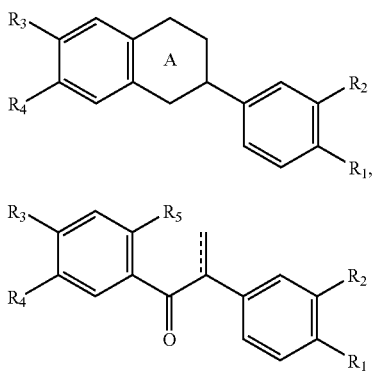

(IB)

(IIB)

wherein A is as defined hereinabove
$R_1$ and $R_2$ are each OH;
$R_4$ is H, and $R_3$ is selected from OH and $OCH_3$;
$R_5$ is selected from OH and $OCH_3$; and
----- denotes a single or double bond.

Examples of preferred compounds of the invention are:
(i) 4',6,7-trihydroxydihydroisoflavone having the structure (III):

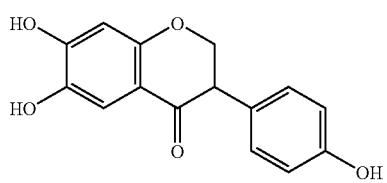

(III)

(hereinafter referred to as Compound B);

5-hydroxy-O-demethylangolesin (5-hydroxy-O-Dma) [1-(2,4,5-trihydroxyphenyl)-2-(4-hydroxyphenyl)-propan-1-one] having the structure (IV):

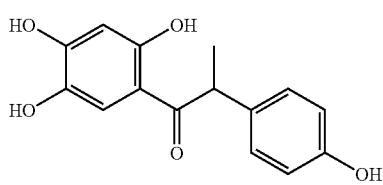

(IV)

(hereinafter referred to as Compound A);

3'-hydroxy-O-demethylangolesin (3'-hydroxy-O-Dma) [1-(2,4,dihydroxyphenyl)-2-(3,4-dihydroxyphenyl)-propan-1-one] having the structure (V):

(V):

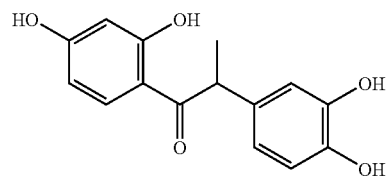

3'-hydroxy-O-demethyldehydroangolesin (3'-hydroxydehydro-O-Dma) [1-(2,4-di-hydroxyphenyl)-2-(3,4-dihydroxyphenyl)-prop-2-en-1-one] having the structure (VI):

(VI)

3'-hydroxy-dihydrodaidzen having the structure (VII):

(VII):

5-hydroxy-2-dehydro-O-Dma[1-(2,4,5-trihydroxyphenyl)-2-(4-hydroxyphenyl)-prop-2-en-1-one] having the structure (VIII):

(VIII):

or pharmaceutically acceptable salts or prodrugs thereof.

A third aspect of the present invention provides a composition comprising one or more compounds of the formulae I or II as previously defined, in association with one or more pharmaceutically acceptable carriers, adjuvants, diluents and/or excipients.

Typically, one or more of the compounds of structures (III) to (VIII) may be used in a composition of the third aspect of the present invention.

A fourth aspect of the present invention is a food or drink composition, which contains one or more compounds of the formulae I or II.

Typically, the food or drink composition contains one or more of the compounds of structures (III) to (VIII).

According to a fifth aspect of the present invention there is provided a method for the treatment, prophylaxis, amelioration, defence against, and/or prevention of menopausal syndrome including depression, anxiety, hot flushes, night sweats, mood swings, and headache; osteoporosis; rheumatic diseases; atherosclerosis; premenstrual syndrome, including fluid retention, cyclical mastalgia, and dysmenorrhoea; coronary artery spasm; vascular diseases including Reynauds Syndrome; Buergers Disease; migraine headaches; hypertension; benign prostatic hypertrophy; all forms of cancer including breast cancer, endometrial cancer, prostatic cancer, uterine cancer, ovarian cancer, testicular cancer, large bowel cancer; Alzheimers disease; inflammatory diseases including Crohns disease, inflammatory bowel disease, ulcerative colitis; baldness including male pattern baldness; psoriasis; acne; and diseases associated with oxidant stress including myocardial infarction, sunlight induced skin damage, arthritis, or cataracts, which method comprises administering to a subject a therapeutically effective amount of one or more compounds of the formulae I or II as previously defined, either alone or in association with one or more pharmaceutically acceptable carriers, diluents, adjuvants and/or excipients.

According to a related sixth aspect of the present invention there is provided a method for the treatment, prophylaxis, amelioration, defence against, and/or prevention of hormone-dependent conditions including hormone dependent cancers such as breast cancer, hormone dependent cardiovascular disorder and hormone dependent menopausal disorders comprising administering to a subject a therapeutically effective amount of one or more compounds of the formulae I or II as previously defined, either alone or in association with one or more pharmaceutically acceptable carriers, diluents, adjuvants and/or excipients.

Typically, one or more of the compounds of structures (III) to (VIII) may be used in the method of treatment, prophylaxis, amelioration, defence against, and/or prevention of any one or more of the diseases of the fifth or sixth aspects of the invention.

A seventh aspect of the present invention is the use of one or more compounds of the formulae I or II for the manufacture of a medicament for the treatment, amelioration, defence against, prophylaxis and/or prevention of one or more of the diseases set out in the fifth or sixth aspects of the invention above.

It is typical that one or more of the compounds of structures (III) to (VIII) are employed in the seventh aspect of the present invention.

A related eighth aspect of the present invention is use of one or more compounds of the formulae I or II in the treatment, amelioration, defence against, prophylaxis and/or prevention of one or more of the diseases set out in the fifth or sixth aspects of the invention above.

Typically, one or more of the compounds of structures (III) to (VIII) are used in the eighth aspect of the invention.

A ninth aspect of the present invention is a microbial culture or a food or drink composition containing at least one microbial strain which microbial strain is capable of producing one or more compounds of the formulae I or II from daidzein and/or glycitein.

Typically, said microbial strain produces one or both of compounds A and B.

Typically, the microbial strain is in the form of a purified culture, which may optionally be admixed and/or administered with one or more other cultures which produce any one or more compounds of the formulae I or II, more typically one or more of the compounds of structures (III) to (VIII).

A tenth aspect of the present invention provides a process for producing a compound of any one of formulae I or II by microbial fermentation of daidzein or glycitein with one or more microbial organisms selected from the group consisting of *Lactobacilli*; *Clostridium perfingens*; Bacteroids including *B. vulgatus, B. thetaiotaomicron, B. distasonis*; *Candida albicans* and other yeast; Anaerobic cocci including *Ruminococcus, Eubacterium, Peptostreptococcus* (such as *P. productus* found in stools), *Clostridium*, Bifidobacteria (such as *B. adolescentis, B. infantis,* and *B. longum*), *Peptococcus, Veillonella, Acidaminococcus,* and *Streptococcus*; Anaerobic streptococci; Gram-negative facultative bacteria; *Aeromonas* such as *A. hydrophila*; *Alcaligenes* sp; *Citrobacter* sp; *Enterobacter* sp including *E. liquefaciens* and *E. aerogenes*; *Escherichia* sp, *E coli*; *Hafnia* sp; *Klebsiella* sp; *Morganella* sp such as *M. morganii*; *Proteus* sp; *Pseudomonas* sp; *Providencia* sp; *Aerococcus viridans*; *Bacillus* sp; *Corynebacterium* sp; *Micrococcus* sp such as *M. luteus*; *Nocardia* sp; *Pediococcus* sp; *Staphylococcus* sp including *S aureus* and *S. epidermidis*; *Fusobacterium* including *F. gonidiaformans, F. mortiferum, F. necrogenes, F. necroforum* and *F. russii*; *Butyrivibrio* such as *B. fibrisolvens*; *Actinomyces*; *Arachnia-Propionibacterium*; *Arthrobacter* sp such as *A. agilis, A. aurescens, A. pascens, A. oxydans, A. nicotinae* and *A. cummins*; *Brevibacterium* sp such as *B. epidermidis*; and *Microbacterium* sp such as *M. arborescens*.

An eleventh aspect of the present invention provides a method for the treatment, prophylaxis, amelioration, defence against, and/or prevention of menopausal syndrome including depression, anxiety, hot flushes, night sweats, mood swings, and headache; osteoporosis; rheumatic diseases; atherosclerosis; premenstrual syndrome, including fluid retention, cyclical mastalgia, and dysmenorrhoea; coronary artery spasm; vascular diseases including Reynauds Syndrome; Buergers Disease; migraine headaches; hypertension; benign prostatic hypertrophy; all forms of cancer including breast cancer, endometrial cancer, prostatic cancer, uterine cancer, ovarian cancer, testicular cancer, large bowel cancer; Alzheimers disease; inflammatory diseases including Crohns disease, inflammatory bowel disease, ulcerative colitis; baldness including male pattern baldness; psoriasis; acne; and diseases associated with oxidant stress including myocardial infarction, sunlight induced skin damage, arthritis, or cataracts, which method comprises administering to a subject a therapeutically effective amount of Factor 2 as previously defined, either alone or in association with one or more pharmaceutically acceptable carriers, diluents, adjuvants and/or excipients.

According to a related twelfth aspect of the present invention there is provided a method for the treatment, prophylaxis, amelioration, defence against, and/or prevention of hormone-dependent conditions including hormone dependent cancers such as breast cancer, hormone dependent cardiovascular disorder and hormone dependent menopausal disorders comprising administering to a subject a therapeutically effective amount of Factor 2 as previously defined, either alone or in association with one or more pharmaceutically acceptable carriers, diluents, adjuvants and/or excipients.

The invention also provides in a thirteenth aspect the use of Factor 2 for the manufacture of a medicament for the treatment, prophylaxis, amelioration, defence against, and/or prevention of menopausal syndrome including depression, anxiety, hot flushes, night sweats, mood swings, and headache; osteoporosis; rheumatic diseases; atherosclerosis; premenstrual syndrome, including fluid retention, cyclical mastalgia, and dysmenorrhoea; coronary artery spasm; vascular diseases including Reynauds Syndrome; Buergers Disease; migraine headaches; hypertension; benign prostatic hypertrophy; all forms of cancer including breast cancer, endometrial cancer, prostatic cancer, uterine cancer, ovarian cancer, testicular cancer, large bowel cancer; Alzheimers disease; inflammatory diseases including Crohns disease, inflammatory bowel disease, ulcerative colitis; baldness including male pattern baldness; psoriasis; acne; and diseases associated with oxidant stress including myocardial infarction, sunlight induced skin damage, arthritis, or cataracts.

A fourteenth aspect of the invention further provides the use of Factor 2 for the manufacture of a medicament for the treatment, prophylaxis, amelioration, defence against, and/or prevention of hormone-dependent conditions including hormone dependent cancers such as breast cancer, hormone dependent cardiovascular disorder and hormone dependent menopausal disorders.

A fifteenth aspect of the present invention provides a process for the manufacture of Compound A, said process including:
  i) reacting 2-(p-methoxyphenyl)propionic acid with 1,3,4-trimethoxy benzene to obtain 2,4,5,4'-tetramethoxy-α-methyldesoxybenzoin; and
  ii) demethylating said 2,4,5,4'-tetramethoxy-α-methyldesoxybenzoin to form 2,4,5,4'-tetrahydroxy-α-methyldesoxybenzoin.

A sixteenth aspect of the present invention provides a compound when produced by the process of the fifteenth aspect of the invention outlined above.

The present invention is based upon the identification of novel oestrogenic isoflavone metabolite compounds, exemplified by the isoflavonoid phytoestrogens of structures (III), (IV) and (V). These compounds have been identified in the urine of the human adult consuming a diet rich in phytoestrogen content. While not wishing to be bound by theory, it is postulated by the present inventor that the identification of the compounds of structures (III), (IV) and (V) provides evidence for the existence of a previously undiscovered pathway in the mode of metabolism of daidzein and/or glycitein.

The identification of the compounds of structures (III), (IV) and (V) observed for the first time in the urine of adult humans who ingested soya cake containing daidzein, genistein and glycitein provides evidence to suggest that the compounds of structures (III), (IV) and (V) are products of microbial transformations of daidzein or glycitein. In view of the fact that one of these metabolites, namely compound A, was found in large amounts commensurate to the amount of daidzein ingested compared with glycitein appears that compounds A and B may also be metabolites of daidzein after hydroxylation of ring A. The results of Klus and Barz (1995) referred to above support this hypothesis since these authors demonstrated that a number of microbial species (*Micrococcus, Arthrobacter, Brevibacterium*) are capable of convening daidzein and glycitein to give Factor 2, the most probable precursor of compounds A and B.

The compounds of Formulae I and II of the present invention, all of which include a vicinal diol substitution, show significant therapeutic activity. In particular, it has been shown that compounds of the invention inhibit the proliferation of MCF-7 and other cells without significant enhancement of their growth al low concentrations. The vicinal diol substitution is provided by at least one of the following: 6,7-dihydroxy substitution in the benzopyran moiety of structure (I); 3',4'-dihydroxy substitution in the 3-phenyl substituent in structure (I); or 3,4-dihydroxy substitution and/or 3',4'-dihydroxy substitution in structure (II). In is speculated that it is the presence of this vicinal diol substitution in the compounds of the invention which confers on them their surprisingly high biological activity.

DETAILED DESCRIPTION OF THE INVENTION

Compounds of the invention may be obtained by microbial fermentation of suitable naturally-occurring oestrogenic isoflavones, or by chemical synthesis.

For microbial fermentation, a plant source of naturally-occurring oestrogenic isoflavones is typically used.

Typically, plant sources for oestrogen isoflavone precursors of the compounds of the invention are any leguminous plant including various species of *Acacia*, ground nut, alfalfa, lentil and ground pea. Also typically, such plant sources include:

*Trefolium* species including *parnassi, repens, pallescens, nigrescens, physodes, resupinatum, campestre, arvense, stellatum, cherleri, pignantii, alpestre, pratense, angustifolium, subterraneum* and *glomeratum*, *Medicago* species including *lupulina, falcata, orbicularis, polymorpha, disciformis, minima*, and *sativa*, *Cassia* species including *occidentalis* and *floribunda*, *Lupinus* species including *angustifolium* and *albus*, *Vivia* species including *sativa* and *monantha* and *Galega* species including *officinalis*, or mutant strains of any one the foregoing. Beans such as jumping bean, sword bean, broad bean, yam bean, kidney bean, soya bean and butter bean are also a favourable source of for oestrogen isoflavone precursors of the compounds of the invention. The oestrogenic isoflavones are mainly found in the leaves and fruit of the plant, and also in the roots.

Typically, the compounds of interest which are secreted by microbial cultures or organisms are detected by GC-MS (gas chromatography-mass spectrometry).

These organisms are used in microbial fermentation to produce compounds of formulae I-II given above. Typically, the organisms are selected from one of the following classes:

*Lactobacilli; Clostridium perfingens*; Bacteroids including *B. vulgatus, B. thetaiotaomicron, B. distasonis; Candida albicans* and other yeast; Anaerobic cocci including *Ruminococcus, Eubacterium, Peptostreptococcus* (such as *P. productus* found in stools), *Clostridium*, Bifidobacteria (such as *B. adolescentis, B. infantis*, and *B. longum*), *Peptococcus, Veillonella, Acidaminococcus*, and *Streptococcus*; Anaerobic streptococci; Gram-negative facultative bacteria; *Aeromonas* such as *A. hydrophila; Alcaligenes* sp; *Citrobacter* sp; *Enterobacter* sp including *E. liquefaciens* and *E. aerogenes*; *Escherichia* sp. *E coli; Hafnia* sp; *Klebsiella* sp; *Morganella* sp such as *M. morganii; Proteus* sp; *Pseudomonas* sp; *Providencia* sp; *Aerococcus viridans; Bacillus* sp; *Corynebacterium* sp; *Micrococcus* sp such as *M. luteus; Nocardia* sp; *Pediococcus* sp; *Staphylococcus* sp including *S aureus* and *S. epidermidis; Fusobacterium* including *F. gonidiaformans, F. mortiferum, F. necrogenes, F. necroforum* and *F. russii; Butyrivibrio* such as *B. fibrisolvens; Actinomyces, Arachnia-Propionibacterium; Arthurobacter* sp such as *A. agilis, A. aurescens, A. pascens, A. oxydans, A. nicotinae* and *A. cummins; Brevibacterium* sp such as *B. epidermidis*; and *Microbacterium* sp such as *M. arborescens*.

Typically, non-pathogenic organisms selected from the above organisms such as *Micrococcus* sp and *Arthrobacter* sp may be used directly in food and/or drink compositions such as dairy formulations so as to provide compounds of the formulae of the invention. The drink/food compositions also need to contain a phytoestrogen source such as soya.

Microbial conversion of Daidzein and Glycitein to Factor-2 can be effected using the following microbial organisms: *Arthrobacter* including *agilis, aurescens, pascens, oxydans, nicotinae*, and *cumminsii*; *Brevibacterium epidermidis* (converts glycitein to Factor 2); *Micrococcus luteus* (converts glycitein to Factor 2), *Microbacterium arborescens* (converts daidzein to Factor 2 & glycitein), *Streptomyces* sp *roseolus* (converts daidzein/glycitein to 8,3'-dihydroxy-6,7,4-trimethoxyisoflavone or daidzein/glycitein to 7,8,4' & 7,3'4'-trihydroxyisoflavones, depending on culture medium). The various microbial conversions are disclosed in detail in Klaus, K. and Barz, W.; *Arch. Microbiol.* 164 (1995) 428-434; Klaus. K., Borger-Papendorf, G. and Barz, W.; *Biochemistry* 34(4) (1993) 979-981; Mackenbrock, K and Barz, W.; *Naturforsch.* 38c (1983) 708; Chimura, H. et al; *J. Antibiot.* 28 (1975) 619-626; Funayama, S. et al; *J. Antibiot.* 42 (1989) 1350-1355 and Komiyama, K. et al; *J. Antibiot.* 42 (1989) 1344-1349, the contents of all of which are incorporated herein by reference.

Without wishing to be bound by theory, the present inventor hypothesises that the metabolic pathways of catabolism of factor 2 obtained from glycitein or daidzein are as shown in Scheme 1 below. Methylene unit (MU) values of the metabolites under the gas chromatographic conditions described in Example 1 are shown.

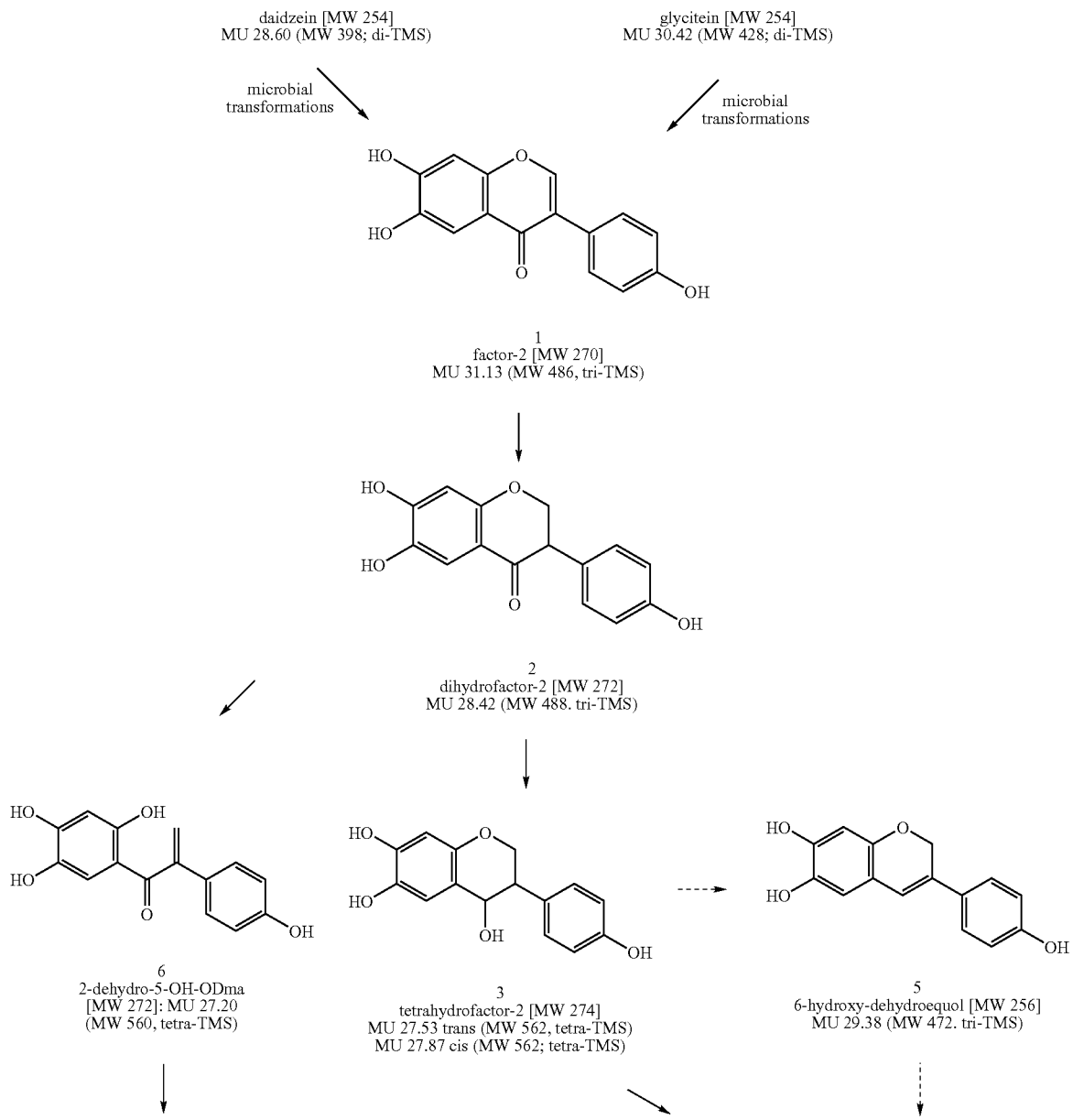

SCHEME 1

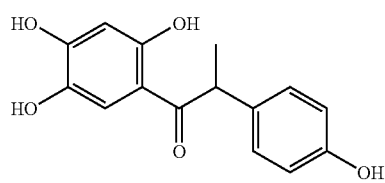

4
5'-hydroxy-ODma
[MW 274] MU 26.12
(MW 520, tetra-TMS)

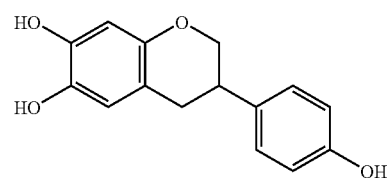

7
6-hydroxy-equol [MW 258]
MU 28.08 (MW 474, tri-TMS)

An alternative source of compounds of the present invention is chemical synthesis. Conveniently, Factor 2 or a naturally-occurring isoflavone such as glycitein may be utilised as starting material. Schemes 2A and 2B demonstrate possible synthesis pathways of compounds of the invention utilising glycitein as the starting material. In Scheme 2A, compounds 2 and 4 may be obtained from glycitein by reduction with lithium aluminium hydride as described in Example 1. A mixture of compounds 3, 5 and 7 identified Scheme 2A may be obtained from compound 8 as shown in Scheme 2B.

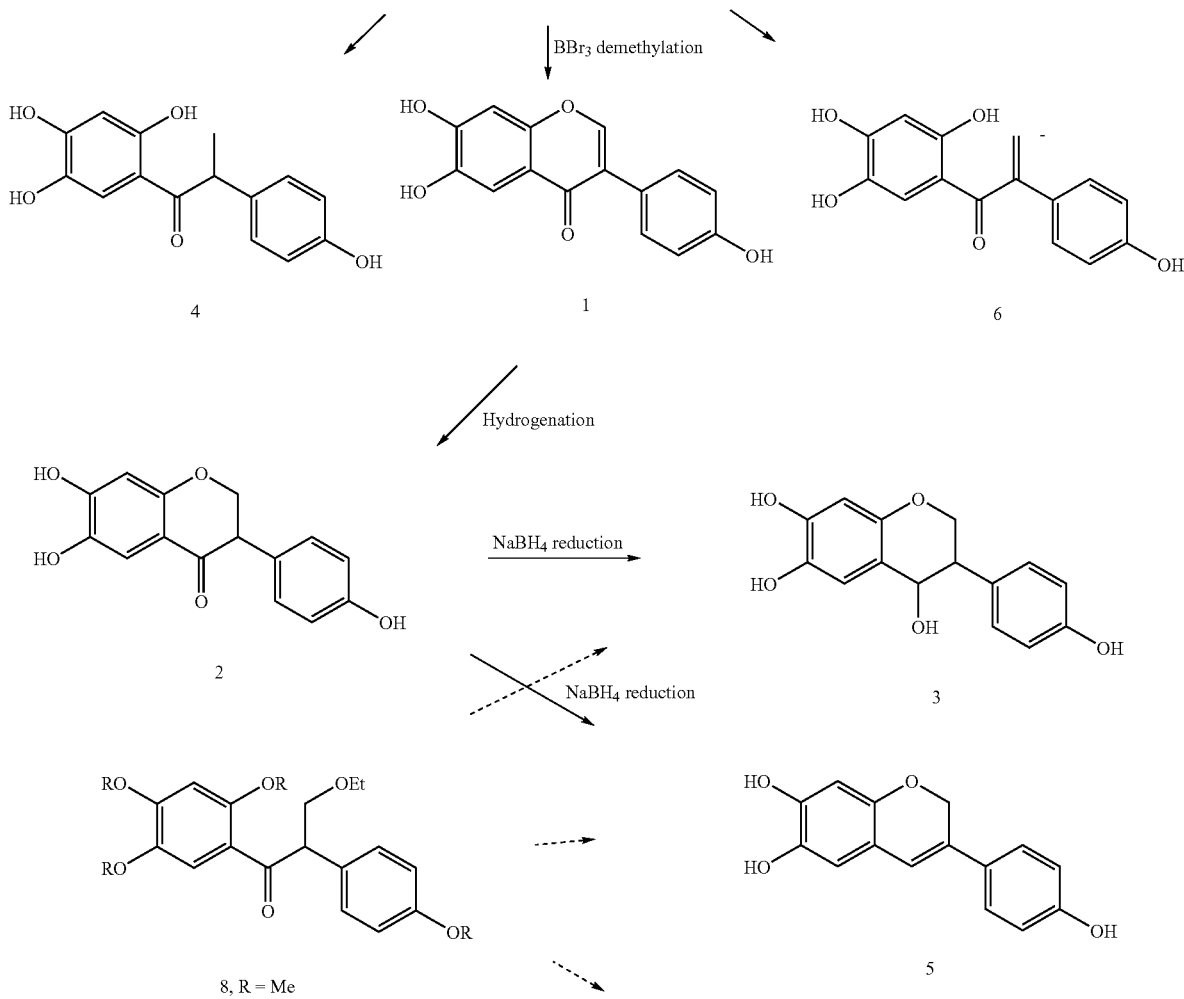

-continued

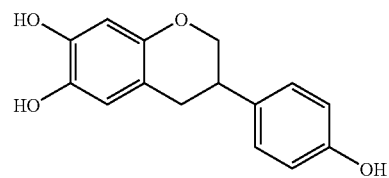

7

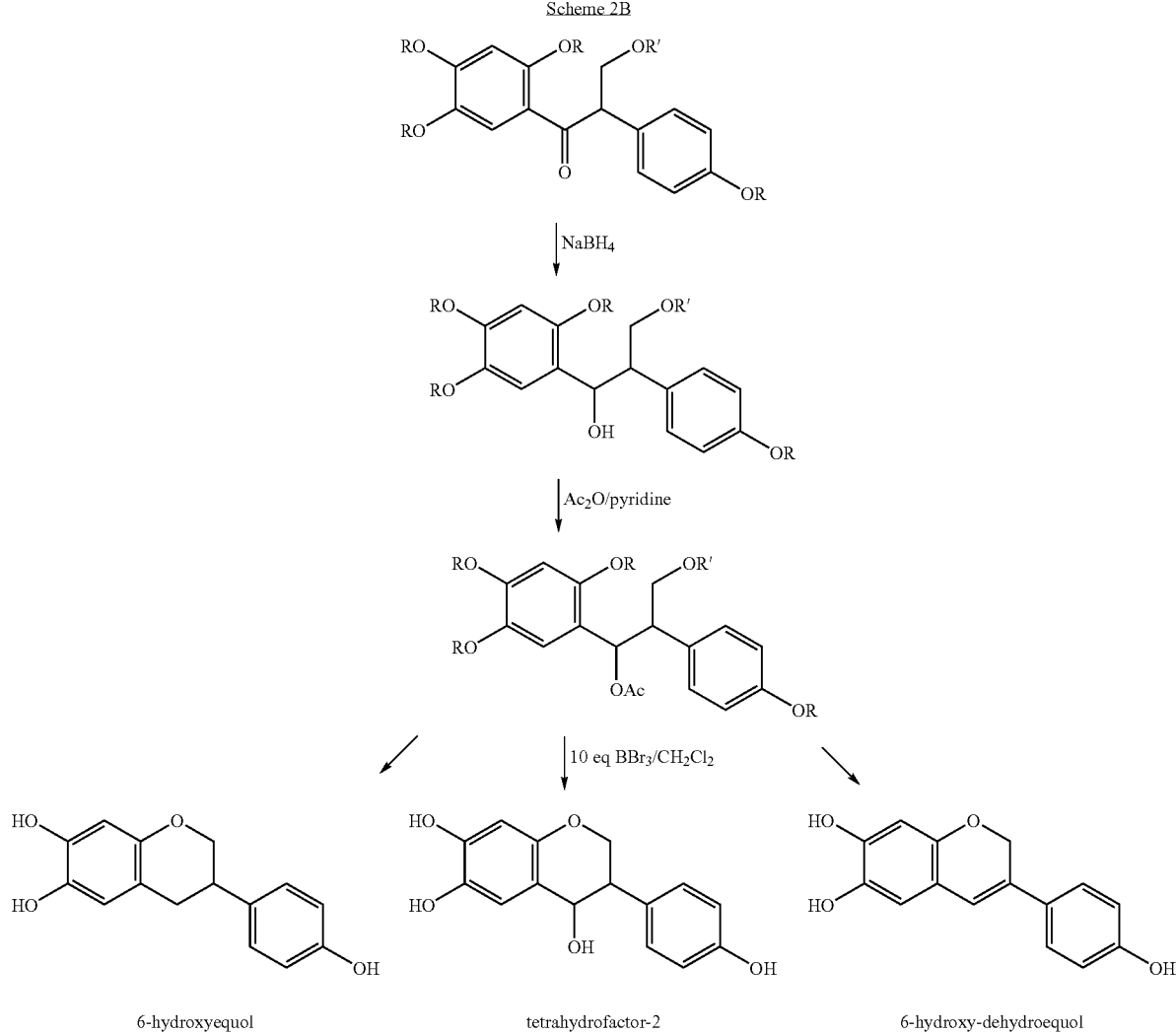

Compounds of the equol or dehydroequol series may also be prepared from the corresponding dihydroisoflavone (exemplified by compound 2 in Scheme 2a) by reduction of the carbonyl and dehydration of the resulting alcohol to give a compound of the dehydroequol series, and optionally catalytically hydrogenating the double bond in the pyran ring to yield the corresponding compound of the equol series.

Unlike the isoflavonoid metabolites of the daidzein and genistein series, those of glycitein have the synthetic advantage that the vicinal hydroxy groups in the A-ring allow a number of protective functional groups such as the ketals and boronates to be formed easily. In the scheme (Scheme 3) below, the synthesis of compounds of Formula II is demonstrated using a 1,2,4-benzenetriol substrate which has been protected as an n-butyl boronate derivative formed using commercially available n-butylboronic acid according to methods adopted in similar protective reactions [Joannou, G. E. and Reeder, A. Y., *Steroids* 61 11-17. (1996)]. Other alkyl boronates can be used.

Scheme 3
Synthesis of 4' Methoxy-5-Hydroxy-O-Dma and similar molecules

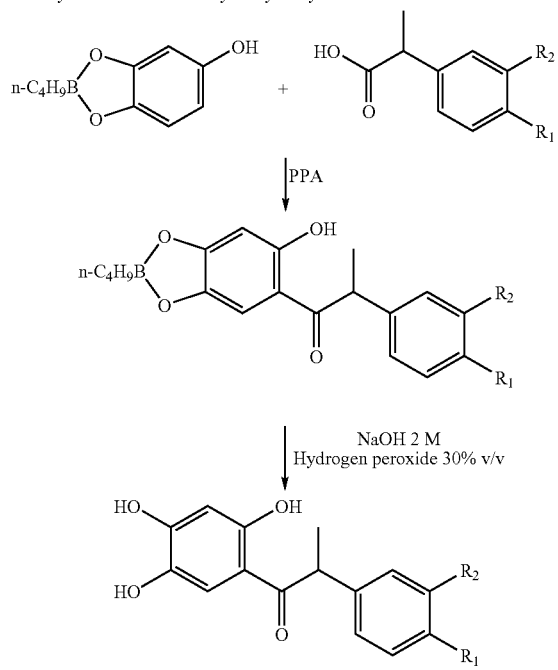

In Scheme 3, one of $R_1$ and $R_2$ is H, OH or $OCH_3$ and the other is OH or $OCH_3$. For the synthesis of compounds of Formula II in which $R_1$ is $OCH_3$, the free hydroxyl group in the boronate intermediate shown above may be methylated, for example by reaction with methyl iodide or methyl sulfate. It will be appreciated that when $R_1$ or $R_2$ is OH, it may require protection. When $R_1$ and $R_2$ are both OH, they may be protected as a cyclic boronate, ketal or carbonate.

Instead of using n-butylboronic acid, formation of protective functional groups may alternatively be achieved using cyclic carbonates, cyclic acetals or ketals as shown in Scheme 4A below. Partial methylation can also be used as shown in Scheme 4B below. Other protective groups for catechols are described in Chapter 3 of Greene, T. W. and Wuts, P. G. M.; Protective Groups in Organic Synthesis ($2^{nd}$ Edition) (1991) John Wiley & Sons, Inc. USA; the disclosure of which is incorporated herein by reference. Compounds of the invention in which $R_1$ is H and $R_2$ is OH or $OCH_3$ or in which $R_1$ and $R_2$ are both OH or $OCH_3$ may be synthesised by analogous procedures to that shown in Scheme 4A but starting with 2-(3-methoxyphenyl)propanoic acid or 2-(3,4-dimethoxyphenyl)propanoic acid instead of the corresponding 4-methoxyphenyl derivative. Similarly, compounds of formula (II) in accordance with this invention, in which one of $R_3$ and $R_4$ is H, may be prepared by an analogous procedure beginning with reaction of resorcinol or hydroquinone, suitably protected, with polyphosphoric acid.

Scheme 4A
Cyclic carbonates, Acetals or Ketals

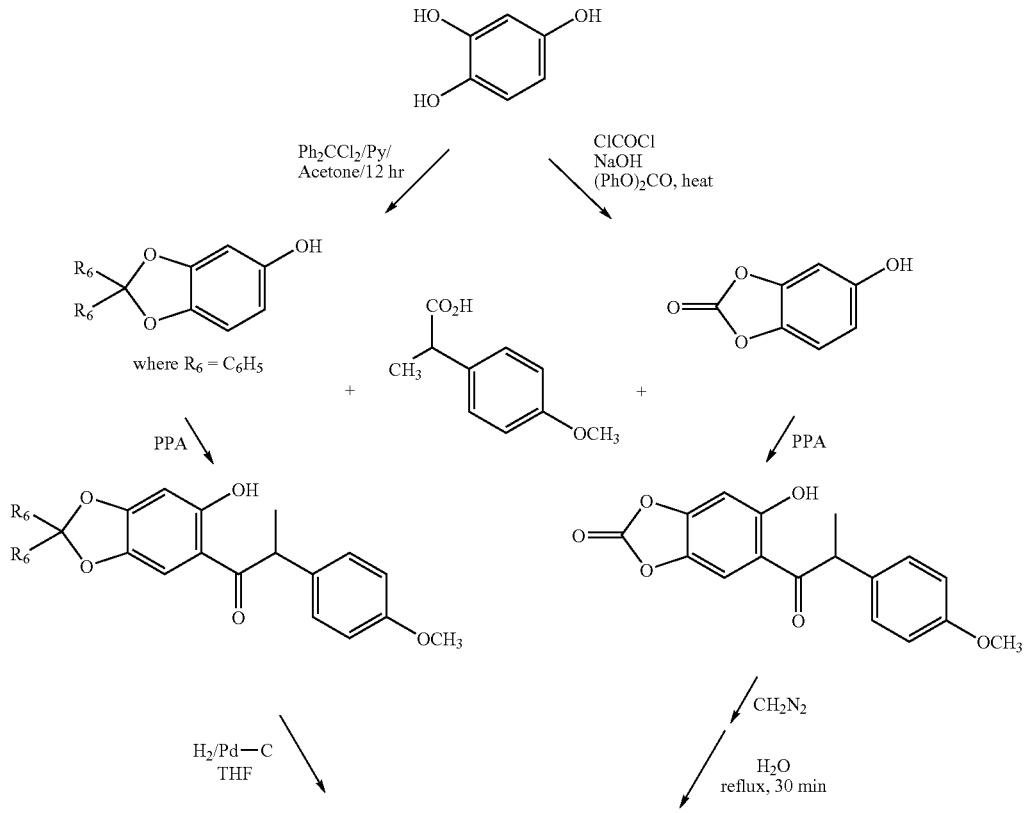

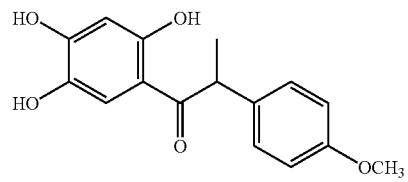
Scheme 4B
Synthesis of 4′-Methoxy Factor-2 and 2′-Methoxy-and 4′-Methoxy-Compound A
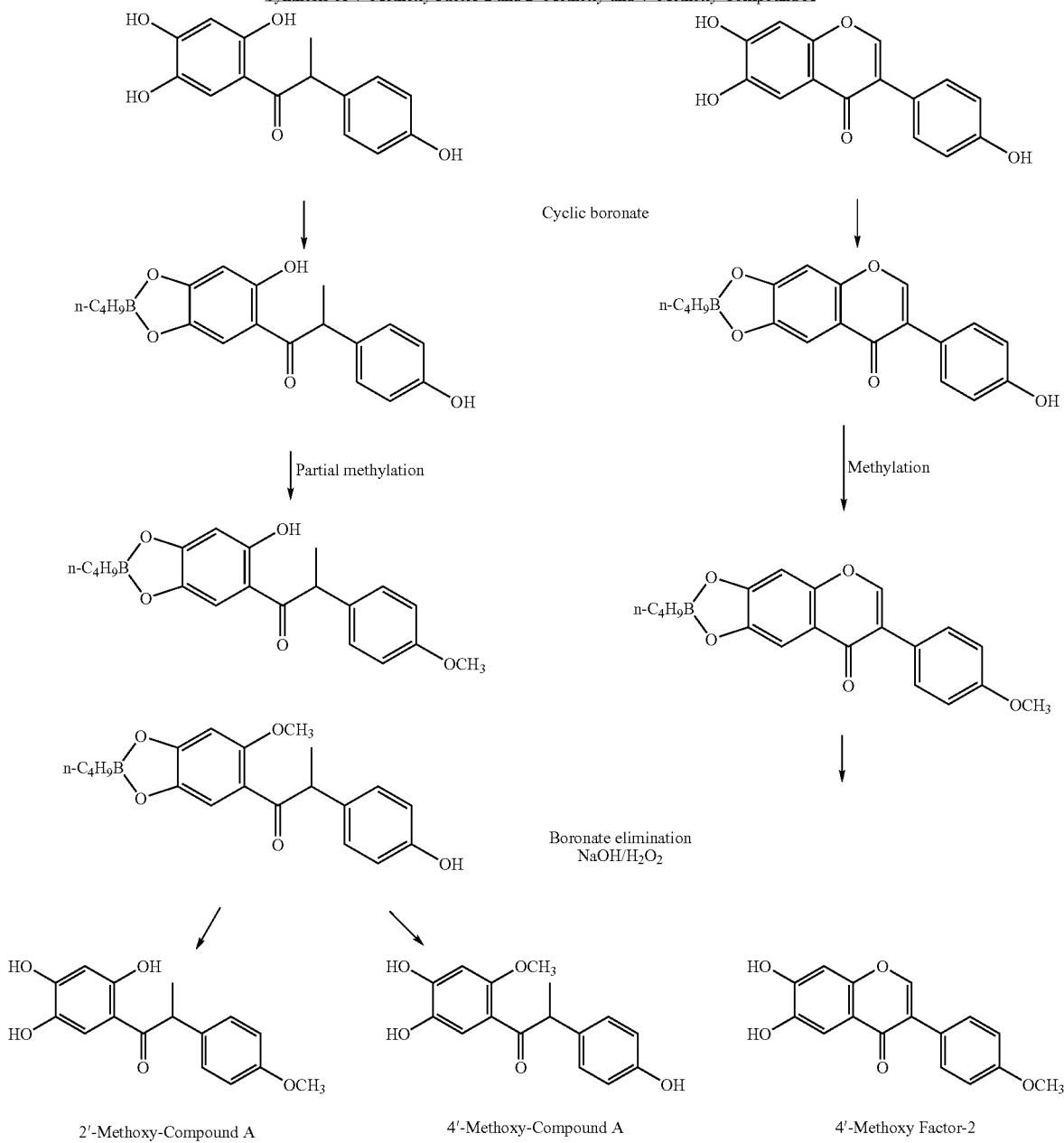

Furthermore formation of cyclic protective groups such as those described above will allow the synthesis of a number of the isoflavonoid compounds proposed which are normally difficult to obtain synthetically as in the case of the tetrahydro, dehydro and equol analogues of glycitein or its demethylated analogues. A schematic representation (Scheme 5) is given below using 4',6,7-trihydroxyglycitein as an example.

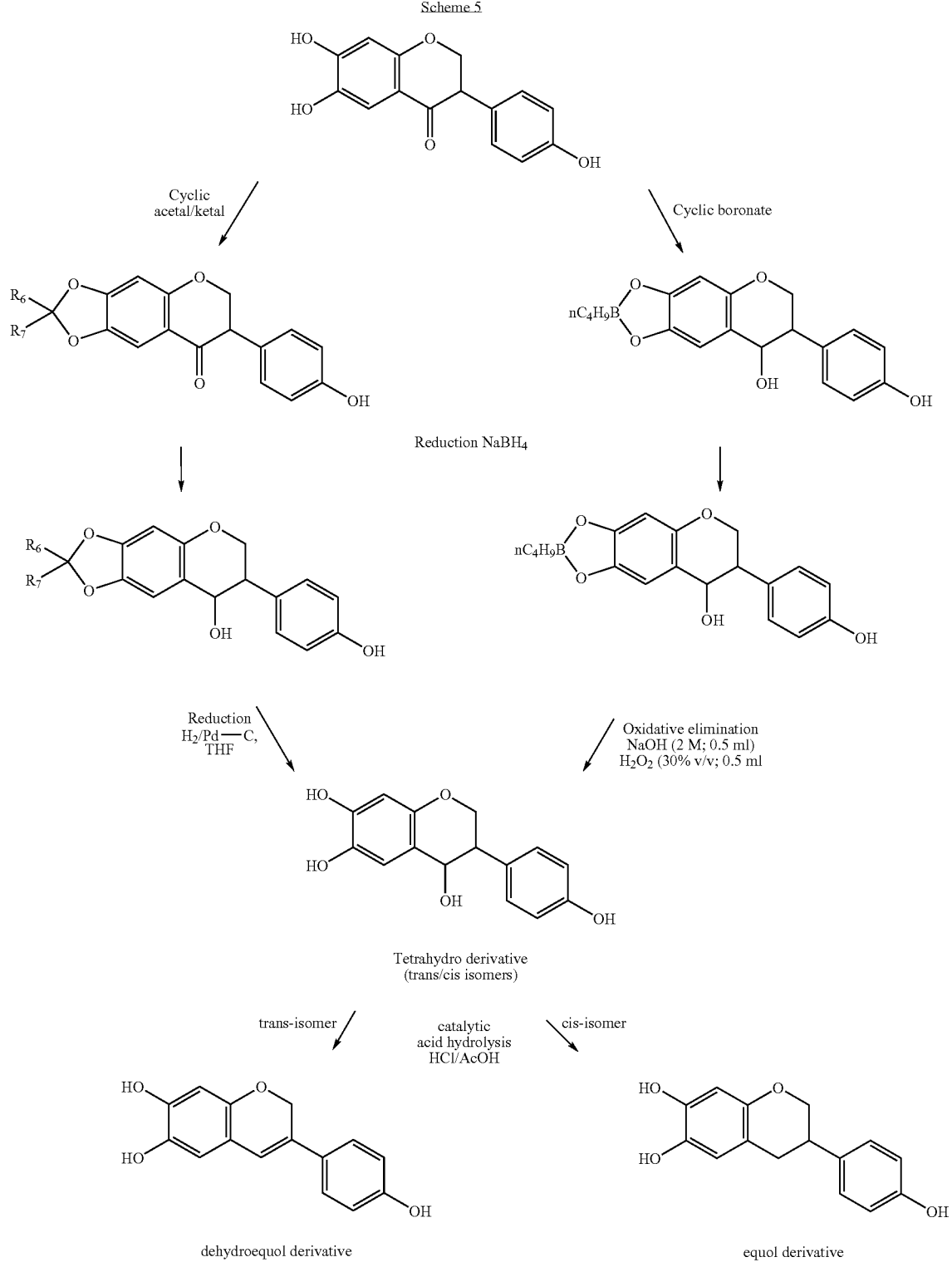

When necessary, hydroxyl groups in the compounds shown in Schemes 1-5 above, may be methylated and/or protected and deprotected, to give other compounds of formula I or II. Suitable protecting groups are described in the work of Greene and Willis referenced above.

Compound A may be prepared by the following synthetic scheme 6:

Scheme 6

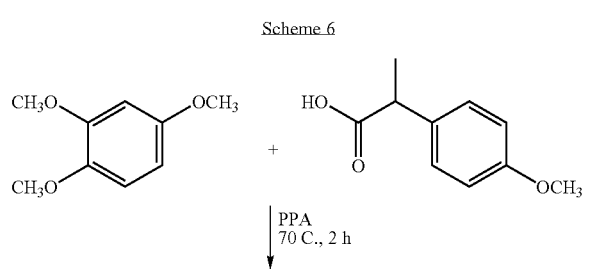

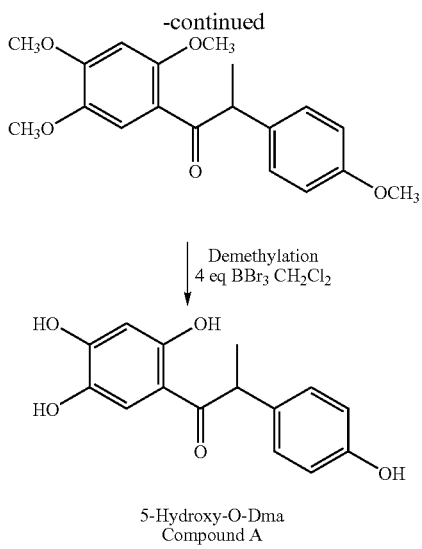

5-Hydroxy-O-Dma
Compound A

Compound B and related compounds of formula (I) or (II) may be prepared as shown in Scheme 7, in which R is $CH_3$, R' is $C_2H_5$, $R_1$-$R_4$ are each H, OH or $OCH_3$, and $R'_1$-$R'_4$ are each H or OH, subject to the proviso that in the final product of formula (I) or (II) $R'_1$ and $R'_2$ are both OH and/or $R'_3$ and $R'_4$ are both OH.

Scheme 7

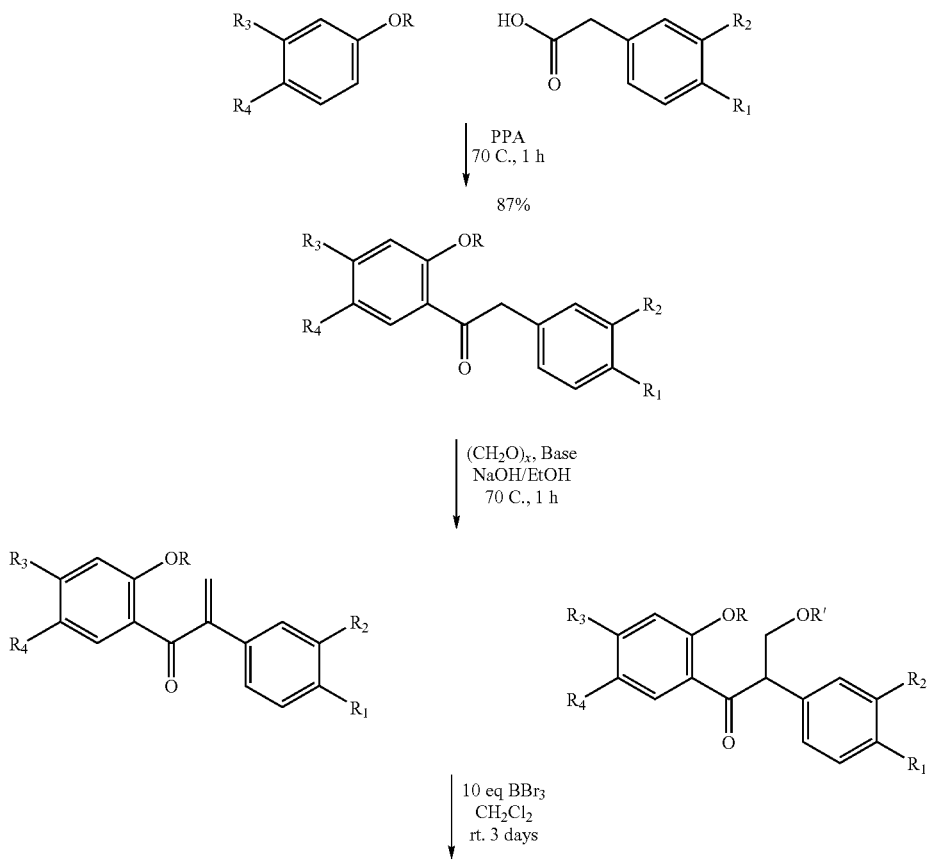

-continued

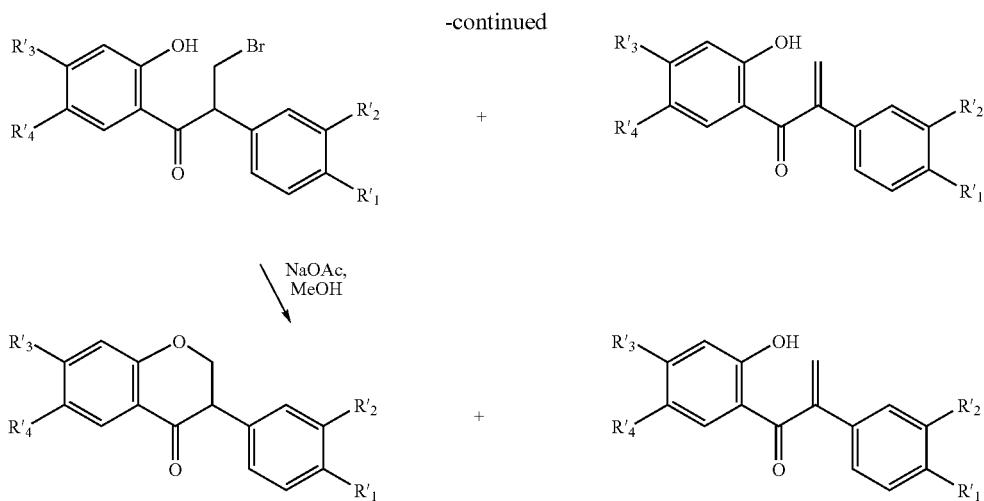

In the above Scheme 7, the base is typically an organic amine, such as dimethylamine, or an alkali metal hydroxide, carbonate or bicarbonate.

In the synthesis of 4',6,7-trihydroxyisoflavone (5-deoxydihydroglycitein) shown in Scheme 7 above, the two intermediates obtained in the penultimate step prior to the demethylation with $BBr_3$ are not easily separated. However, it was found that a simple recrystallization procedure using methanol/water provided a quick method of separation and purification of the two intermediates. A similar procedure may be applied to the isolation of the methylated precursors of daidzein and genistein, namely formononetin and biochanin A, which are present in clover and soya. Complete methylation of formononetin and biochanin A may further enhance the process of recrystallization of these two isoflavonoid precursors. Isolated formononetin or its fully methylated analogue can be used as a substrate for the chemical or microbial transformations to give Factor 2 or any of the compounds of Formula I or II defined above.

As an example, formononetin or its methylated analogue may be isolated from a rich source such as clover or soya for subsequent microbial transformation to Factor 2 or a compound of formula I or II. Alternatively, isolates of clover extracts containing formononetin and daidzein may be fermented to produce Factor 2 or its methylated analogue for extraction with water and/or an organic solvent. As a further possibility, Factor 2 and compounds of formula I or II, may be obtained by chemical transformation of formononetin, daidzein, glycitein or other naturally-occurring isoflavones as described in more detail above.

The compounds of the formulae I or II, or Factor 2, may be administered in a manner as is generally known in the art. The dosage utilised will depend upon a number of factors including the specific application, the condition being treated, the mode of administration, the state of the subject, the route of administration and the nature of the particular compound used.

Typically, a daily dose amount of a compound of the invention, such as any of the compounds of structures (III) to (VIII) which is required in a therapeutic treatment according to the invention, is in the range of 0.1 mg to 2 g; more typically from 0.5 mg to 1 g; even more typically from 50 mg to 500 mg; most typically from 50 to 250 mg.

In the production of a pharmaceutical composition of the present invention any one or more of the compounds of formulae I or II, or Factor 2, is/are typically admixed with one or more pharmaceutically acceptable carriers, adjuvants, diluents and/or excipients as are well known in the art.

The carrier must, of course, be acceptable in the sense of being compatible with any other ingredients in the composition and must not be deleterious to the subject. The carrier or excipient may be a solid or a liquid, or both, and is preferably formulated with the compound as a unit-dose, for example, a tablet, which may contain from 0.5% to up to 100% by weight of die active compound.

Typically, one or more of die compounds of structures (III) to (VIII) may be incorporated in the compositions of the invention, which may be prepared by any of the well known techniques of pharmacy consisting essentially of admixing the components, optionally including one or more accessory ingredients.

The compositions of the invention are typically formulated to include those suitable for rectal, optical, oral, buccal, parenteral (for example, subcutaneous, intramuscular, intradermal, or intravenous) and transdermal administration, although the most suitable route in any given case will depend on the nature and severity of the condition being treated and on the nature of the particular active compound which is being used.

For parenteral administration, the compound(s) of the invention may be prepared in sterile aqueous or oleaginous solution or suspension. Suitable non-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example.

Compositions of die invention may be prepared by means known in the art for the preparation of compositions (such as in the art of preparing veterinary and pharmaceutical compositions) including blending, grinding, homogenising, suspending, dissolving, emulsifying, dispersing and where appropriate, combining or mixing of the compound(s) of any of Formulae I or II, or Factor 2 together with the selected excipient(s), carrier(s), adjuvant(s) and/or diluent(s).

Compositions formulated as suitable for oral administration may be presented in discrete units, such as capsules, cachets, lozenges, or tablets, each containing a predetermined amount of the preferred active compound; as a solution or a suspension in an aqueous or non-aqueous liquid; as a powder or granules; or as an oil-in-water or water-in-oil emulsion. For example, compressed tablets may be prepared by compressing any one or more compounds of formulae I or II, or Factor 2, in a free-flowing form, such as a powder or granules, optionally mixed with a binder, lubricant, inert diluent, and/or surface active/dispersing agent(s). Moulded tablets may be made by moulding, in a suitable machine, a powdered compound of any one of formulae I or II, or Factor 2, moistened with an inert liquid binder.

Solid forms for oral administration may contain pharmaceutically or veterinarily acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents, include polymers or copolymers of acrylic acid and/or methacrylic acid and/or their esters, waxes, fatty alcohols, zein, shellac or gluten. Suitable preservatives include sodium benzoate, vitamin E. alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxy-methylcellulose, methylcellulose, hydroxypropylmethyl-cellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as gum acacia or gum tragacanth.

For parenteral administration, the active compound(s) of Formulae I or II or Factor 2 may be prepared in sterile aqueous or oleaginous solution or suspension. Suitable non-toxic parenterally acceptable diluents or solvents include water, Ringer's solution, isotonic salt solution, 5% dextrose in water, buffered sodium or ammonium acetate solution, 1,3-butanediol, ethanol, propylene glycol or polyethylene glycols in mixtures with water. Aqueous solutions or suspensions may further comprise one or more buffering agents. Suitable buffering agents include sodium acetate, sodium citrate, sodium borate or sodium tartrate, for example. These preparations suitable for parenteral administration, are preferably administered intravenously, although administration may also be effected by means of subcutaneous, intramuscular, or intradermal injection. Aqueous solutions for parenteral administration are also suitable for administration orally or by inhalation.

Typical parenterally administered preparations may conveniently be prepared by admixing one or more of the compounds of structures (III) to (VIII) with water or a glycine buffer and rendering the resulting solution sterile and isotonic with the blood. Injectable formulations according to the invention generally contain from 0.1% to 70% w/v of active compound and are typically administered at a rate of 0.1 ml/minute/kg.

For rectal administration, the compound(s) of Formulae I or II or Factor 2 is suitably administered in the form of an enema or unit dose suppository. A suitable suppository may be prepared by mixing the active substance with a non-irritating excipient which is solid at ordinary temperatures but which will melt in the rectum. Suitable such materials are cocoa butter, waxes, fats, glycerol, gelatin and polyethylene glycols. Suitable enemas may comprise agents as exemplified above with reference to forms for topical administration.

Suitably, an inhalation spray comprising a compound(s) of Formulae I or II or Factor 2 will be in the form of a solution, suspension or emulsion as exemplified above. The inhalation spray composition may further comprise an inhalable propellant of low toxicity. Suitable propellants include carbon dioxide or nitrous oxide.

The pharmaceutical composition may contain pharmaceutically acceptable binders, diluents, disintegrating agents, preservatives, lubricants, dispersing agents, suspending agents and/or emulsifying agents as exemplified above. The veterinary composition may contain veterinarily acceptable binders, diluents, disintegrating agents, preservatives, lubricants, dispersing agents, suspending agents and/or emulsifying agents as exemplified above.

The invention includes compositions which are used for topical application which may be a cream, ointment, paste, solution, emulsion, lotion, milk, jelly, gel, spray, aerosol, oil, stick, roll-on or smooth-on, wherein the active compound comprises up to about 90%, more typically 10%, by weight of the composition, even more typically from about 0.1% to about 5% by weight, for example 3.5% by weight, even more typically from 0.5% to 2% w/w, and the compositions include topically suitable carriers, diluents, excipients, adjuvants and other additives.

Illustrative of pharmaceutically or cosmetically topically acceptable carriers or diluents are demineralized or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysiloxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropyl-methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the composition.

Adjuvants typically include emollients, emulsifiers, thickening agents, preservatives, bacteriocides and buffering agents.

Emollients suitable for inclusion in a topical composition of the invention include fatty esters such as isopropyl myristate, cetyl acetate, diisopropyl adipate or $C_{12}$-$C_{15}$ alcohol benzoates; fatty alcohols such as lauryl alcohol, myristyl alcohol, cetyl alcohol, stearyl alcohol or cetostearyl alcohol; mineral and vegetable oils such as, aloe vera and jojoba oil; lecithin; Vitamin E; lanolin; sorbitol and glycerin. Typically, the emollient or emollients will form from 10% to 99.9% by weight of the composition.

Suitable thickening agents include sodium stearate, calcium stearate, magnesium stearate, calcium palmitate and magnesium palmitate, dextran, dextrins, starch and starch products, gelatin, cellulose derivatives as exemplified above, collagen, water soluble polymers such as carboxyvinyl polymer, polyvinyl alcohol or polyvinyl acetate, pectin, xanthan gums, bentonite, hyaluronic acid fumed silica and the like. Typically, the thickening agent or agents will form from 0.1% to 20% by weight of the composition.

Typical preservatives include ascorbic acid and its salts, erythorbic acid and its salts, ethyl and iso-propyl p-hydroxybenzoates, benzalkonium chloride, benzyl alcohol, phenylethanol and glydant chlorobutanol. Typically, the preservative or preservatives will form from 0.1% to 12% by weight of the composition.

Suitable buffering agents are salts of boric, acetic, phosphoric, citric, malic, silicic acids and the like, for example sodium citrate, sodium bicarbonate, sodium acetate and sodium phosphate. Additionally or alternatively, the free acids may be used, together with an alkali such as sodium hydroxide, sodium carbonate, sodium bicarbonate, potassium hydroxide, potassium carbonate or potassium bicarbonate. Typically, the buffering agent or agents will form from 0.1% to 20% by weight of the composition.

Emulsifiers may also be included in a topical composition of the invention. Illustrative nonionic emulsifiers include fatty acids such as oleic acid, stearic acid and palmitic acid; esters of lactic acid, tartaric acid, ascorbic acid or citric acid; polyalkylene glycol esters such as polyoxyethylene glycol monostearates, polyoxyethylene glycol monolaurates; polyoxyethylene glycol distearates or polyoxyethylene glycol dilaurates; polyalkylene glycol ether derivatives of aliphatic or cycloaliphatic alcohols such as polyoxyethylene nonylphenol ether, polyoxyethylene cetyl ether or polyoxyethylene stearyl ether; hexitan esters, for example sorbitan monolaurate, sorbitan monooleate, sorbitan distearate, sorbitan tristearate, sorbitan dilaurate or sorbitan trilaurate; fatty esters such as glyceryl monostearate, ethylene glycol monostearate, propylene glycol monostearate or butylene glycol monostearate; sorbitol and ethoxylated sorbitol esters of fatty acids such as polyoxyethylene sorbitan monostearate, polyoxyethylene sorbitan monolaurate, polyoxy-ethylene sorbitan monooleate, polyoxyethylene sorbitan distearate, polyoxyethylene sorbitan dilaurate, polyoxyethylene sorbitan dioleate, polyoxyethylene sorbitan tristearate, polyoxyethylene sorbitan trilaurate or polyoxyethylene sorbitan trioleate; long-chain alcohols such as lauryl, myristyl, stearyl, oleyl, cetyl or cetostearyl alcohol; polysaccharides such as starch and starch derivative, cellulose derivatives as exemplified above, agar, tragacanth, acacia and alginic acid; and steroidal derivatives such as lanolin alcohols or ethoxylated lanolin alcohols, and beeswax. Illustrative ionic surfactants include triethanolamine and amine soaps such as triethanolamine stearate; anionic soaps such as calcium or magnesium salts of stearic acid or palmitic acid; fatty alcohol sulfates, for example sodium lauryl sulfate; alkyl or aralkyl sulfanates such as sodium sulfosuccinates or sodium dodecylbenzene-sulfonate; quaternary ammonium salts containing at least one long-chain alkyl group as N-substituent, for example stearyl trimethylammonium chloride, and phosphate esters of polyalkylene glycols. Typically, the emulsifier or emulsifiers will form from 0.1% to 99% by weight of the composition.

The topical compositions of the invention may further include a sunscreen. Suitable sunscreens include opacifiers such as titanium dioxide or zinc oxide; p-aminobenzoic acid, isobutyl p-aminobenzoate, glyceryl p-aminobenzoate, or N-substituted derivatives of p-aminobenzoic acid such as isoamyl p-dimethylaminobenzoate, pentyl p-dimethylamino-benzoate, octyl p-dimethylaminobenzoate or ethyl 4-[bis(2-hydroxypropyl)amino]benzoate; 2-hydroxy-1,4-naphthoquinone; octocrylene; octyl p-methoxycinnamate or 2-ethoxyethyl p-methoxycinnamate; salicylate esters such as octyl salicylate, homomethyl salicylate or 2-[bis(2-hydroxyethyl)-amino]ethyl salicylate; oxybenzone and methyl anthranilate. Typically, the sunscreen or sunscreens will form from 0.1% to 10% by weight of the composition.

Additionally, it will be understood that the topical compositions of the invention may include suitable colouring agents and/or perfumes well known in the art. Typical examples of suitable perfuming agents are provided in S. Arctander, "Perfume and Flavor Chemicals", Montclair. N.J., 1969.

Formulations suitable for transdermal administration are typically presented as discrete patches adapted to remain in intimate contact with the epidermis of the recipient for a prolonged period of time. Such patches suitably contain at least one compound of formulae I or II, or Factor 2, preferably one or both of compounds A and B, as an optionally buffered aqueous solution of, for example, 0.1M to 0.5M concentration with respect to the said active compound. More typically, one or both of compounds A and B are present in a concentration of 0.1-0.3M concentration.

The active compounds of formulae I or II may be provided in the form of food and/or drink compositions, such as being added to, admixed into, coated or combined with a food or drink product.

Typically, food and drink compositions of the present invention are dairy based. More typically, one or more of compounds of structures (III) to (VIII) are combined or otherwise formulated into a dairy based food or drink product such as a milk drink or supplement, and a chilled or frozen dairy product such as a dairy based dessert.

Therapeutic methods, uses and compositions may be for administration to humans or animals, including domestic animals, birds (including chickens, turkeys, ducks), livestock animals (such as cattle, sheep, pigs and goats) and the like.

It will be appreciated that the examples referred to above are Illustrative only and other suitable carriers, diluents, excipients and adjuvants known to the art may be employed without departing from the spirit of the invention.

Embodiments of the invention will now be described with reference to the following non-limiting Examples.

EXAMPLE 1

5-hydroxy-O-demethylangolensin (Compound A)
[1-(2,4,5-trihydroxyphenyl)-2-(4'-hydroxyphenyl)-propan-1-one]

1. As Product of Lithium Aluminium Hydride Reduction Reaction from Glycitein

Glycitein (20.16 mg, $0.75 \times 10^{-7}$ mol) was weighed out and dried under vacuum. The dried glycitein was dissolved in anhydrous THF (~3.0 ml) and to this solution 10 eq of $LiAlH_4$ (1.0 M in ether) was added dropwise at room temperature. The reaction was allowed to stir at room temperature overnight, then refluxed for 5 hr. After workup the solution was filtered through celite using methanol. The filtrate was concentrated and analysed by GC and HPLC ($MeOH/H_2O$ 40:60). Among the products separated by GC those at MU 25.69 and 28.65 were the major ones. After isolation of the two major products by preparative HPLC, these were analysed by GC-MS characterising them as derivatives of Compounds A and B respectively. Demethylation of these products was achieved by boron tribromide in dichloromethane at room temperature for three days according to Bannwart C et al., (*Finn. Chem. Lett.* 1984, Vol 11, p 120). In performing the GC-MS, a 30 metre SE30 capillary column was used with temperature program of 200-230° C. at increments of 2° C./min, and 230-280° C. at increments of 10° C./min. The carrier gas was helium.

2. As a Product of Acylation Reaction

Step 1: Formation of 2,4,5,4'-tetramethoxy-α-methyldesoxybenzoin. To a mixture of 2-(p-methoxyphenyl)propionic acid (0.20 g, 1.11 mmol) and polyphosphoric acid (5 gm), 1,3,4-trimethoxy benzene (0.186 g, 1.11 mmol, 0.166 ml) was added. The mixture was allowed to heat to 75° C. while stirring for 6 hours. TLC (30% EtOAc:Hexane) and gas chromatography (GC) and gas chromatography-mass spectrometry (GC-MS) analyses confirmed the presence of two major products with MU values of 24.68 and 25.01 (ratio 1:4). Chromatography on silica column (30% EtOAc:Hexane) allowed the isolation of the two products. Product MU 24.92 was isolated as a crystalline low melting solid. NMR data and GC-MS data confirmed the above structure. A 42% and 11% yield was obtained for products MU 25.01 and MU 24.68 respectively.

Step 2: Formation of 2,4,5,4'-tetrahydroxy-α-methyldesoxybenzoin. The product 2,4,5,4'-tetramethoxy-α-methyldesoxybenzoin (MU 25.01; 0.063 g) obtained from Step 1 above was dissolved in anhydrous dichloromethane (30.0 mL) and boron tribromide (0.271 g. 1.08 mmol) was added to the solution. The mixture was allowed to stir at room temperature for 24 hours under nitrogen. TLC (30% EtOAc:hexane) established the presence of a single product which on GC analysis as the trimethylsilyl ether gave a single peak at MU 26.01. After workup with ice/water the product was extracted with diethyl ether, washed with water, dried and concentrated to give a crude yellow oil, which by NMR and GC-MS data was confirmed to be 2,4,5,4'-tetrahydroxy-α-methyldesoxybenzoin.

Mass Spectra Data (EIMS: Electron Ionisation; CIMS: Chemical Ionization; High Resolution: HR)

HR: 274.084267, theoretical 274.084267.

EIMS: m/z (% rel int) 274 [M]+ (14). 153 (100); 121 (29). 77(8).

EIMS as the tetra-trimethylsilyl derivative: 562(1.6); 547 (4.7); 457(1.6); 369(100); 281 (6.7); 193 (5.4); 147 (2.7).

CIMS as the tetra-trimethylsilyl derivative: M+1=563(75); 547(59); 491(15); 370 (31); 369(100); 193(22).

NMR Data $^1$H n.m.r.

(Acetone-d6, 2.05 ppm) δ 1.39 (3H, d, J=7.2 Hz, $CH_3$), 4.62 (1H, q, J=7.2 Hz, CH). 6.29 (1H, s, ArH-3). 6.75 (2H, d, J=9.2 Hz, ArH-3',5'). 7.17 (2H, d, J=9.2 Hz, ArH-2',6'). 7.33 (1H, s, Ar-6) 8.73

$^{13}$C n.m.r.

(Acetone-d6, ppm) 18.73, 45.59, 103.05, 110.845, 115.38, 115.58, 128.51, 132.96, 137.60, 153.86, 156.25, 159.85, 204.77.

UV: $\lambda_{max}$=283 nm

EXAMPLE 2

5-deoxydihydroglycitein (Compound B)

Compound B was obtained in a series of reactions as illustrated in Scheme 7, involving an acylation reaction, formation of an α-alkenyl ketone and cyclisation/demethylation. In brief, 2,4,5-trimethoxyphenyl-4'-methoxybenzyl ketone was obtained as an intermediate in an acylation reaction using 1,2,4-trimethoxybenzene (5.9 mmol), 4-methoxyphenylacetic acid (5.9 mmol) and polyphosphoric acid (17 gm) after heating at 70° C. for one hour with mechanical stirring. Potassium carbonate was then added to the reaction for another one and half hours. The crude product was purified by recrystallization from ethyl acetate and light petroleum to give light yellow crystals (75% yield). The α-alkenyl ketone was subsequently obtained by a modification of Gandhidasan's method (Gandhidasan R et al., *Synthesis*, 1982, 1110). In brief, to a suspension of 2,4,5-trimethoxyphenyl-4'-methoxybenzyl ketone in ethanol, para-formaldehyde and N,N-dimethylamine was added and the mixture was allowed to reflux while heated for one hour. When the reaction was complete, the precipitate was filtered and the filtrate was concentrated in vacuo, after which the residue was dissolved in ethyl acetate and washed with water. The organic layer was dried with magnesium sulphate and filtered, and the solvent was removed to give the crude product. On purification by flash chromatography two compounds were obtained in 57% yield. Fractional recrystallization of the mixture gave 1-(4-methoxyphenyl)-1-(2,4,5-trimethoxybenzoyl)ethylene as the major product (~41%) and α-ethoxymethyl-2,4,5-trimethoxyphenyl-4'-methoxybenzyl ketone as the minor product (~17%). The method provided the best yields when 1% potassium bicarbonate is used instead of the dimethylamine in the methylation step.

When sodium hydroxide was used instead the percentage yield was lower namely 38% and 14% respectively for these two products. The desired dihydro product Compound B (6,7,4'-trihydroxyisoflavone) was finally obtained by demethylation of 1-(4-methoxy-phenyl)-1-(2,4,5-trimethoxybenzoyl)ethylene using boron tribromide in dichloromethane at room temperature for three days according to Bannwart C et al., *Finn. Chem. Lett.* 11 120 (1984) followed by cyclisation of the resulting brominated intermediate by sodium acetate in methanol.

In the formation of the α-alkenyl ketone in the absence of a base the reaction will not proceed and the starting material will remain unchanged. The good yield of this method provides a good chemical method for the synthesis of a number of the dihydro derivatives of daidzein, genistein or glycitein.

Mass Spectra Data (EIMS Electron Ionisation; CIMS Chemical Ionization; High Resolution HR)

Compound B: HR: 272.0673 theoretical 272.0673

EIMS: m/z (% rel. int.) 272 [M]+ (31), 244 (9); 168(7); 153 (100); 120 (40); 107 (27); 91 (11).

CIMS: 301 M+29 (14); 273 M+1 (52); 257 (37); 137 (23); 97 (17); 83 (45); 71 (100).

EIMS as the tri-trimethylsilyl derivative: MU 28.48. MW 488; 488 (14); 473 (7); 369 (30); 296 (100); 281 (9); 192 (27); 177 (24); 147 (9).

NMR Data $^1$H n.m.r. (Acetone-d6) δ 2.05 ppm (1H, dd. $J_{3.2eq}$=9.5. Hz, H-3), 4.14 (1H, dd. $J_{2ax,2eq}$=9.7 Hz, J $J_{2ax,3}$=9.6 Hz, $H_{2ax}$), 4.99 (1H, dd. $J_{2eq,2ax}$=9.8 Hz, J 2eq, 3=4.9 Hz, $H_{2eq}$), 6.38 (1H, s, ArH-8). 6.82 (2H, d. J=8.6 Hz, ArH-3',5'), 7.27 (2H, d, J=8.6 Hz, ArH-2',6'), 7.46 (1H, s, ArH-5).

$^{13}$C n.m.r. (Acetone-d6, 29.8 ppm) δ 33.5, 54.6, 103.9, 111.9, 116.6, 128.4, 129.3, 138.78, 155.2, 158.0, 160.4, 201.8.

UV: $\lambda_{max}$=284 nm

EXAMPLE 3

1(2,4-dihydroxyphenyl)-2-(3',4'-dihydroxyphenyl)-1-oxo-2-propene (3'-hydroxy-O-demethyldehydroangolesin); structure (VI)

1. 1-(2,4-dihydroxyphenyl)-2-(3', 4'-dihydroxyphenyl)-1-oxo-ethane

A mixture of 1,3-dimethoxybenzene (2.00 g, 14.47 mmol) and 3,4-diemthoxyphenylacetic acid (2.84 g, 14.47 mmol) in polyphosphoric acid was heated at 80° C. for 2 hours. After cooling, the mixture was poured onto ice water and the water was extracted with ethyl acetate (50 mL). The combined organic phases were washed with water, sodium bicarbonate solution and water and dried over anhydrous magnesium sulfate. Evaporation of the solvent gave light yellow crystals of 1-(2,4-dihydroxyphenyl)-2-(3',4'-dihydroxyphenyl)-1-oxo-ethane which were purified by recrystallisation.

2. 1-(2,4-dimethoxyphenyl)-2-(3',4'-dimethoxyphenyl)-1-oxo-2-propene and 1-(2,4-di-methoxyphenyl)-2-(3',4'-dimethoxyphenyl)-1-oxo-3-ethoxy-propane A mixture of the product of step 1 (3.504 g, 11.08 mmol), 95% paraformaldehyde (1.275 g, 46.66 mmol) and N,N-dimethylamine (5.6 mL, 46.66 mmol) in ethanol (58 mL) was heated under reflux for one hour. Then potassium carbonate (1.612 g, 11.67 mmol) was added to the mixture and heating under reflux was continued for a further three hours after which the precipitate was removed by filtration and the solvent was removed under reduced pressure. The residue was dissolve in ethyl acetate and the solution was washed with water, 0.2M HCl and water, dried over magnesium sulfate and concentrated to give a yellow oil. 1-(2,4-dimethoxyphenyl)-2-(3',4'-dimethoxyphenyl)-1-oxo-2-propene was separated from 1-(2,4-dimethoxyphenyl)-2-(3',4'-dimethoxyphenyl)-1-oxo-3-ethoxy-propane by column chromatography with a mobile phase of 40% ethyl acetate in hexane.

3. 1-(2,4-dihydroxyphenyl)-2-(3',4'-dihydroxyphenyl)-1-oxo-2-propene 0.406 g (1.08 mmol) of 1-(2,4-dimethoxyphenyl)-2-(3',4'-dimethoxyphenyl)-1-oxo-3-ethoxy-propane were reacted with boron tribromide (10.84 mmol) in 22 mL dichloromethane for three days by the method of Bannwart C. et al. *Finn. Chem. Lett.* 11 120 (1984). Workup and chromatography of the reaction product afforded 1-(2,4-dihydroxyphenyl)-2-(3',4'-dihydroxyphenyl)-1-oxo-2-propene as the minor product and 1-(2,4-dihydroxyphenyl)-2-(3',4'-dihydroxyphenyl)-1-oxo-3-bromo-propane as the major product.

Mass spectral data (electron impact) for 1-(2,4-dihydroxyphenyl)-2-(3',4'-dihydroxyphenyl)-1-oxo-2-propene as tetra-TMS derivative: m/z (% relative intensity) at 209 (10), 267 (4.5), 281 (100), 545 (20), 560 (23).

EXAMPLE 4

7-hydroxy-(3',4'-dihydroxyphenyl)-2,3-dihydroisoflavone (3'-hydroxy-dihydro-daidzein); structure (VII)

0.157 g of 1-(2,4-dihydroxyphenyl)-2-(3',4'-dihydroxyphenyl)-1-oxo-3-bromo-propane, the major product of step 3 in Example 3, and about 2 molar equivalents of sodium acetate ware mixed with 88 mL of methanol and heated at about 60° C. for 4 hours. After cooling, the mixture was acidified to pH 5 and the methanol was removed under reduced pressure. The residue was dissolved in ethyl acetate (50 mL) and the solution was washed with water and concentrated. The crude product was separated by column chromatography to yield approximately equal amounts of 1-(2,4-dihydroxyphenyl)-2-(3',4'-dihydroxy-phenyl)-1-oxo-2-propene and 7-hydroxy-(3',4'-dihydroxyphenyl)-2,3-dihydroisoflavone.

Mass spectral data (electron impact) for 7-hydroxy-(3',4'-dihydroxyphenyl)-2,3-dihydroisoflavone as tri-TMS derivative: m/z (% relative intensity) at 192 (7.2), 281 (100), 473 (6.6), 488 (17).

EXAMPLE 5

1-(2,4-dihydroxyphenyl)-2-(3',4'-dihydroxyphenyl)-1-oxopropane; structure (V)

The title compound was obtained by catalytic hydrogenation of 1-(2,4-dihydroxyphenyl)-2-(3',4'-dihydroxyphenyl)-1-oxo-2-propene obtained as in Example 3 or Example 4. To a solution of 1-(2,4-dihydroxyphenyl)-2-(3',4'-dihydroxyphenyl)-1-oxo-2-propene in methanol was added palladium on carbon, and hydrogen gas was bubbled vigorously through the solution for ten minutes. Removal of the catalyst and evaporation of the solvent afforded the title compound.

Mass spectral data (electron impact) for 1-(2,4-dihydroxyphenyl)-2-(3',4'-dihydroxyphenyl)-1-oxopropane as tetra-TMS derivative: m/z (% relative intensity) at 209 (5.8), 281 (100), 369 (2.4), 457 (1.2), 459 (1.3), 547 (4.0), 562 (1.2).

EXAMPLE 6

1-(2,4,5-trihydroxyphenyl)-1-(4-hydroxyphenyl)-1-oxo-2-propene (5-hydroxy-2-dehydro-O-Dma); structure (VIII)

This compound was prepared as shown in Scheme 7 utilising methodology analogous to that described in Example 3.

Mass spectral data (electron impact) for 1-(2,4,5-trihydroxyphenyl)-2-(4-hydroxyphenyl)-1-oxo-2-propene as tetra-TMS derivative: m/z (% relative intensity) at 147 (40), 281 (28), 369 (63), 370 (20), 545 (94), 546 (46), 560 (100), 561 (50), 562 (27).

EXAMPLE 7

Bacterial sp and Culture Conditions

The standard incubation assays of bacteria (100 mg wet wt) with isoflavone substrates ($5 \times 10^{-5}$ M), the composition of the mineral salt medium and the isolation of the transformation products from the medium were essentially as described according to Klus, K. et al. *Arch. Microbiol.* 164 428-434 (1995). The mineral medium and micronutrients were used according to Pfennig and Lippert (1966). In summary Bacterial sp were cultivated on Merck Standard I nutrient agar and for incubation experiments for 15 hr in 100 ml Merck Standard I nutrient broth. Prior to incubation the bacteria were washed twice with 200 ml Kpi buffer (0.05M, pH 7.5). After centrifugation (10,000 g, 15 min) 100 mg bacteria (fr. Wt) were inoculated in 5 ml mineral medium and 50 µl substrate solution (DMSO-MeOH, 1:10) was applied to the bacterial culture. Substrate concentration was $5 \times 10^{-5}$. The cultures were incubated in culture tubes (200×16 mm) in an orbital shaker at 200 rpm, 30° C.

EXAMPLE 8

Effects of Isoflavonoid Phytoestrogens on the Induced Growth of MCF-7 Cells and Other Cells Compound A was compared with genistein to test the cell viability of MCF-7 cells. Genistein was known, prior to this invention, to be the most potent individual inhibitor of cancer cells in in vitro experiments. The cell viability was tested using the MTS in vitro cytotoxicity assay. This is considered the most convenient assay because of its ease of use, accuracy and rapid indication of toxicity (Malich G et al., *Toxicology* 124(3): 179-92 (1997).

The results obtained show that at high concentrations (40 micrograms/ml) of each, genistein showed an inhibition at 1, 2, 3 and 6 days of incubation with an IC50 of 32, 22, 15 and 18 micrograms/ml, compared with IC50 values of 6, 6.5 and 7 for Compound A for the same periods respectively. More importantly, Compound A inhibited the growth of MCF-7 cells even at low concentrations, namely 2.5 micrograms/ml and as early as within 8 hours of incubation and at days 1 and 2. By contrast, other isoflavonoids including genistein at concentrations (<10 µM) enhance rather than inhibit the growth of MCF-7 cancer cells.

IC50 values observed for other compounds of the invention against MCF-7 cells were as follows:

| Compound of structure: | IC50 (µg/mL) |
|---|---|
| (IV) | 6-10 |
| (V) | 10-20 |
| (VI) | 3.2 |
| (VII) | about 28 |
| (VIII) | <8 |

The compound of structure (VI) was also tested against PC3 and LNCap cells and the IC50 values observed were 6.2 and 7.0 µg/mL respectively.

EXAMPLE 9

Comparative Inhibitory and Proliferative Effects of Daidzein and Genistein, their Methylated Analogues and Metabolites with 5-Hydroxy-O-Dma (Compound A) on MCF7 Cells In vitro cell tissue culture experiments with MCF7 breast cancer cells when incubated with 5-hydroxy-O-Dma (Compound A) showed significant inhibition as compared with genistein, daidzein or their methylated precursors, namely formononetin and biochanin A or their metabolites for concentrations of 15-40 µg/ml. This variation was more significant when cells were incubated for 8 hours where it was demonstrated that 5-hydroxy-O-Dma had an IC50 of 6 µg/ml as compared with that of genistein which had an IC50 of >40 µg/ml for the same period of incubation. Subsequent incubations at 24 hours, 48 hours, 72 hours and 144 hours revealed that the IC50 value of 5-hydroxy-O-Dma remained basically unchanged: ie remained in the range of 4-7 µg/ml. This is in contrast to the IC50 values obtained for genistein after incubations for 48 hours (IC50=38) and 144 hours (IC50=15 µg/ml).

For concentrations of less than or equal to 10 µM of 5-hydroxy-O-Dma and genistein, no significant inhibition was observed. However, in the case of genistein, some proliferative activity of cancer cells was demonstrated at concentrations of less than or equal to 10 µM, whereas 5-hydroxy-O-Dma showed no proliferative activity of cancer cells.

When daidzein, formononetin, biochanin A and other metabolites of daidzein and genistein such as dihydrodaidzein, tetrahydrodaidzein (transisomer), O-Dma, 6-hydroxy-O-Dma and equol were tested for their inhibitory effect on MCF7 cells, it was found that with the exception of biochanin A and 6-hydroxy-O-Dma which showed some inhibition with an IC50 of 18-23 µg/ml at 72 and 144 hours incubation, all other metabolites had no significant effect, with their IC50 values at about 36->50 µg/ml.

These results suggest that compound A is a potent inhibitor of breast cancer cells but more importantly, compound A showed no proliferative activity of cancer cells at low concentrations as genistein does. The 6,7-dihydroxy groups in compounds of the invention appear to be critical for this difference of biological activity of compounds of the invention when compared with analogues such as O-Dma and 6-hydroxy-O-Dma.

EXAMPLE 10

Comparative Inhibitory Effects of Daidzein and Genistein, their Methylated Analogues and Metabolites with 5-Hydroxy-O-Dma (Compound A) on Breast Cancer Cells 5-Hydroxy-O-Dma when tested with MDA-MB-468 (estrogen negative) cancer cells showed significant inhibition at day 6 (IC50=6.8 µg/ml) as compared with 8.8 µg/ml for genistein and 3-7 times more inhibitive when compared with analogues of daidzein and genistein namely O-Dma (20 µg/ml) and 6-hydroxy-O-Dma (43 µg/ml) respectively. The IC50 of 5-hydroxy-O-Dma using MCF-7 estrogen positive breast cancer cells on day 6 of incubation was 2.1 µg/ml for 5-hydroxy-O-Dma as compared with the analogues of daidzein and genistein namely O-Dma (38 µg/ml) and 6-hydroxy-O-Dma (33 µg/ml) respectively.

These results suggest that inhibition of 5-hydroxy-O-Dma like that of genistein, was more severe for the estrogen negative (−ve) cancer than that of the estrogen positive (+ve) cancer cells which suggests that in both these cases the mechanism of action is not related to the estrogen receptors.

EXAMPLE 11

Inhibitory Effects of Factor-2 on Breast Cancer Cells

Factor 2 was obtained by complete demethylation of glycitein after 4 days of incubation with $BBr_3$. Incomplete demethylation gave a mixture of glycitein and Factor 2. Alternatively, following fermentation of daidzein and glycitein from clover to give Factor-2, selective extraction and/or precipitation of Factor 2 from the fermentation medium can be easily achieved.

Factor-2 when tested with MCF 7 estrogen positive breast cancer cells and MDA-MB-468 (estrogen negative) breast cancer cells showed significant inhibition of both types of cancer cells. Inhibition of MCF-7 cells using Factor 2 gave IC50 values (at day 6 of incubation) of 12 µg/ml and for MDA-MB-468 cells, the IC50 value was 8 10 µg/ml.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

The invention claimed is:

1. The compound having the structure

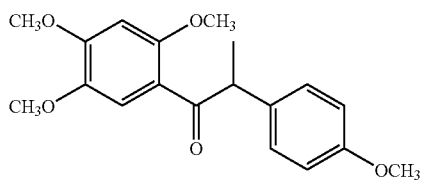

IV or a pharmaceutically acceptable salt thereof.

2. A pharmaceutical composition comprising a compound as claimed in claim 1 in association with at least one of: pharmaceutically acceptable carriers; adjuvants; diluents; and excipients.

3. A food or drink composition which contains at least one compound according to claim 1.

4. The compound having the structure

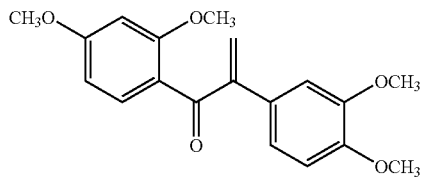

VI or a pharmaceutically acceptable salt thereof.

5. A pharmaceutical composition comprising a compound as claimed in claim 4 in association with at least one of: pharmaceutically acceptable carriers; adjuvants; diluents; and excipients.

6. A food or drink composition which contains at least one compound according to claim 4.

7. The compound having the structure

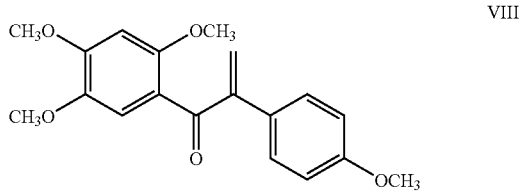

VIII or a pharmaceutically acceptable salt thereof.

8. A pharmaceutical composition comprising a compound as claimed in claim 7 in association with at least one of: pharmaceutically acceptable carriers; adjuvants; diluents; and excipients.

9. A food or drink composition which contains at least one compound according to claim 7.

10. The compound having the structure

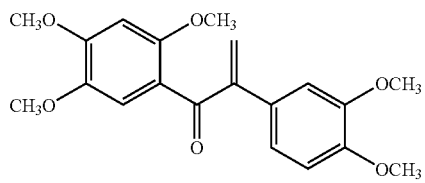

or a pharmaceutically acceptable salt thereof.

11. A pharmaceutical composition comprising a compound as claimed in claim 10 in association with at least one of:
pharmaceutically acceptable carriers; adjuvants; diluents; and excipients.

12. A food or drink composition which contains at least one compound according to claim 10.

* * * * *